(12) United States Patent
Siemionow et al.

(10) Patent No.: US 9,820,747 B2
(45) Date of Patent: Nov. 21, 2017

(54) USE OF EPINEURAL SHEATH GRAFTS FOR NEURAL REGENERATION AND PROTECTION

(75) Inventors: Maria Siemionow, Shaker Heights, OH (US); Krzysztof Siemionow, Shaker Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 263 days.

(21) Appl. No.: 12/935,232

(22) PCT Filed: Apr. 2, 2009

(86) PCT No.: PCT/US2009/039258
§ 371 (c)(1),
(2), (4) Date: Dec. 8, 2010

(87) PCT Pub. No.: WO2009/124170
PCT Pub. Date: Oct. 8, 2009

(65) Prior Publication Data
US 2011/0087338 A1    Apr. 14, 2011

Related U.S. Application Data

(60) Provisional application No. 61/123,026, filed on Apr. 4, 2008.

(51) Int. Cl.
*A61B 17/11* (2006.01)
*A61B 17/32* (2006.01)
*A61B 17/00* (2006.01)

(52) U.S. Cl.
CPC ..... *A61B 17/1128* (2013.01); *A61B 17/32002* (2013.01); *A61B 2017/00349* (2013.01);
(Continued)

(58) Field of Classification Search
CPC .......... A61B 17/1128; A61B 17/32002; A61B 17/28; A61B 17/32; A61B 17/3211;
(Continued)

(56) References Cited

U.S. PATENT DOCUMENTS 4,662,884 A * 5/1987 Stensaas et al. ............. 606/152
4,759,764 A * 7/1988 Fawcett et al. ............... 623/1.1
(Continued)

FOREIGN PATENT DOCUMENTS

EP    1595503 A2    11/2005
EP    2 349 028     8/2011
(Continued)

OTHER PUBLICATIONS 00-14-2010, Notification Concerning Transmittal of International Preliminary Report on Patentability (Chapter 1 of the Patent Cooperation Treaty), PCT/US2009/039258.
(Continued)

*Primary Examiner* — Alexander Orkin
(74) *Attorney, Agent, or Firm* — Saliwanchik, Lloyd & Eisenschenk

(57) ABSTRACT

Described herein is conduit material that causes minimal inflammatory reaction, and serves as a structural guide for regenerating nerve tissue (e.g., axons). Thus, the invention is directed to methods of treating a nerve injury in an individual in need thereof. The methods employ an isolated, naturally occurring epineural sheath, and can be used, for example, to regenerate nerve tissue in an individual in need thereof. Also provided herein is a device for harvesting an epineural sheath.

50 Claims, 20 Drawing Sheets

(52) U.S. Cl.
CPC .............. *A61B 2017/00969* (2013.01); *A61B 2017/320044* (2013.01); *A61B 2017/320064* (2013.01)

(58) Field of Classification Search
CPC ........... A61B 2017/00349; A61B 2017/00969; A61B 2017/320044; A61B 2017/320064
USPC ........................ 623/23.72; 606/152; 424/423
See application file for complete search history.

(56) References Cited

U.S. PATENT DOCUMENTS

| | | | |
|---|---|---|---|
| 4,863,668 A * | 9/1989 | Griffiths et al. | 264/512 |
| 5,085,658 A | 2/1992 | Meyer | |
| 5,122,151 A * | 6/1992 | de Medinaceli | 606/152 |
| 5,577,517 A | 11/1996 | Bonutti | |
| 5,904,690 A * | 5/1999 | Middleman et al. | 606/113 |
| 6,290,718 B1 | 9/2001 | Grooms et al. | |
| 6,436,116 B1 | 8/2002 | Spitz et al. | |
| 2001/0053839 A1* | 12/2001 | Noishiki et al. | 527/300 |
| 2002/0082632 A1 | 6/2002 | Spitz et al. | |
| 2003/0003082 A1 | 1/2003 | Eisenbach-Schwartz et al. | |
| 2003/0040112 A1* | 2/2003 | Muir | 435/368 |
| 2004/0102772 A1 | 5/2004 | Baxter et al. | |
| 2004/0199186 A1* | 10/2004 | Kuffler et al. | 606/152 |
| 2007/0010831 A1* | 1/2007 | Romero-Ortega et al. | 606/152 |
| 2007/0077232 A1 | 4/2007 | Naughton et al. | |
| 2008/0234602 A1 | 9/2008 | Oostman et al. | |
| 2008/0234697 A1 | 9/2008 | DuBois | |
| 2008/0234698 A1 | 9/2008 | Oostman et al. | |
| 2008/0234699 A1 | 9/2008 | Oostman Jr. et al. | |
| 2010/0016874 A1* | 1/2010 | Lieberman | 606/152 |
| 2011/0087338 A1 | 4/2011 | Siemionow et al. | |
| 2012/0020933 A1* | 1/2012 | Young et al. | 424/93.7 |
| 2012/0171172 A1 | 7/2012 | Siemionow et al. | |
| 2015/0320802 A1 | 11/2015 | Siemionow | |

FOREIGN PATENT DOCUMENTS

| | | |
|---|---|---|
| EP | 2 473 193 | 7/2012 |
| WO | WO 2008/115526 A3 | 9/2008 |
| WO | WO 2009/124170 A1 | 10/2009 |
| WO | WO 2011/028814 A1 | 3/2011 |
| WO | WO 2015/138967 A1 | 9/2015 |

OTHER PUBLICATIONS

Archibald, S.J., et al., "A Collagen-Based Nerve Guide Conduit for Peripheral Nerve Repair: An Electrophysical Study of Nerve Regeneration in Rodents and Nonhuman Primates," *The Journal of Comparative Neurology*, 306: 685-696 (1991).
Atabay, K., et al., "The Use of 'Sliding Epineurial Sheath Tube' for Repair of Peripheral Nerve Defects," *Surgical Forum 80th Annual Clinical Congress*: 719-722 (1994).
Ayahan, S., et al., "Use of the Turnover Epineurial Sheath Tube for Repair of Peripheral Nerve Gaps," *Journal of Reconstructive Microsurgery*, 16(5): 371-377 (2000).
Brandt, J., et al., "Autologous Tendons Used as Grafts for Bridging Peripheral Nerve Defects," *The Journal of Hand Surgery*, 24B(3): 284-290 (1999).
Chen, L, et al., "Denatured Muscle as a Nerve Conduit: A Functional, Morphologic, and Electrophysiologic Evaluation," *The Journal of Reconstructive Microsurgery*, 10(3): 137-144 (1994).
Demirkan, F., et al., "A Method of Enhancing Regeneration of Conventionally Repaired Peripheral Nerves," *Annals of Plastic Surgery*, 34(1): 67-72 (1995).
Doolabh, V.B. and Mackinnon, S.E., "FK506 Accelerates Functional Recovery Following Nerve Grafting in a Rat Model," *Plastic and Reconstructive Surgery*, 103(7): 1928-1936 (1999).
Entin, M.A., "Self-Fulfilling Prophecies: Reflections on the Future of A.S.S.H.," *The Journal of Bone and Joint Surgery*, 56A(5): 1088-1097 (1974).

Fox, I.K., et al., "Prolonged Cold-Preservation of Nerve Allografts," *Muscle and Nerve*, 31: 59-69 (2005).
Hall, S., "Nerve Repair: A Neurobiologist's View," *The Journal of Hand Surgery*, 26B(2):129-136 (2001).
Hart, et al., "Pharmacological Enhancement of Peripheral Nerve Regeneration in the Rat by Systemic acetyl-L-carnitine Treatment," *Neuroscience Letters*, 334: 181-185 (2002).
Hazari, A., et al., "A Resorbable Nerve Conduit as an Alternative to Nerve Autograft in Nerve Gap Repair," *British Journal of Plastic Surgery*, 52: 653-657 (1999).
Hu, J., et al., Repair of Extended Peripheral Nerve Lesions in Rhesus Monkeys Using Acellular Allogenic Nerve Grafts Implanted with Autologous Mesecnchymal Stem Cells,: *Experimental Neurology* 204: 658-666 (2007).
Hudson, T.W., et al., "Engineering Strategies for Peripheral Nerve Repair," *Clinics in Plastic Surgery*, 26(4): 617-628 (1999).
Kawakami, M., et al., "Experimental Lumbar Radiculopathy Immunohistochemical and Quantitative Demonstrations of Pain Induced by Lumbar Nerve Root Irritation of the Rat," *Spine*, 19(16): 1780-1794 (1994).
Kelleher, M.O., et al., "The Use of Conventional and Invaginated Autologous Vein Grafts for Nerve Repair by Means of Entubulation," *British Journal of Plastic Surgery*, 54: 53-57 (2001).
Keskin, M., et al., "Enhancement of Nerve Regeneration and Orientation Across a Gap with a Nerve Graft Within a Vein Conduit Graft: A Functional, Stereological, and Electrophysiological Study," *Plastic and Reconstructive Surgery*, 113(5): 1372-1379 (2004).
Kim, B et al., "Peripheral Nerve , Regeneration Using Acellular Nerve Grafts," *J. Biomed Mater Res*, 68A: 201-209 (2004).
Langone, F., et al., "Peripheral Nerve Repair Using a Poly(organo)phosphazene Tubular Prosthesis," *Biomaterials*, 16(5): 347-353 (1995).
Lundborg, G., et al., "Nerve Regeneration Across an Extended Gap: A Neurobiological View of Nerve Repair and the Possible Involvement of Neuronotrophic Factors," *The Journal of Hand Surgery*, 7(6): 580-587 (1982).
Lundborg, G., et al., "Nerve Regeneration in Silicone Chambers: Influence of Gap Length and of Distal Stump Components," *Experimental Neurology*, 76: 361-375 (1982).
Mackinnon, S.E., et al., "A Study of Neurotrophism in a Primate Model," *The Journal of Hand Surgery*, 11A(6): 888-894 (1986).
Mackinnon, S.E., et al., "Clinical Outcome Following Nerve Allograft Transplantation," *Plastic and Reconstructive Surgery*, 107(6): 1419-1429 (2001).
Mackinnon, S.E., "New Directions in Peripheral Nerve Surgery," *Annals of Plastic Surgery*, 22(3): 257-273 (1989).
Martini, A. and Fromm, B., "A New Operation for the Prevention and Treatment of Amputation Neuromas," *The Journal of Bone and Joint Surgery*, 71B(3): 379-382 (1989).
Meirer, R., et al., "Effect of Chronic Cyclosporine Administration on Peripheral Nerve Regeneration: A Dose-Response Study," *Annals of Plastic Surgery*, 49(1): 96-103 (2002).
Meirer, R., et al., "Neurogenic Perspective on Vascular Endothelial Growth Factor: Review of the Literature," *Journal of Reconstructive Microsurgery*, 17(8): 625-629 (2001).
Midha, R., et al., "Growth Factor Enhancement of Peripheral Nerve Regeneration Through a Novel Synthetic Hydrogel Tube," *J. Neurosurg.*, 99: 555-565 (2003).
Mohammad, J., et al., "Modulation of Peripheral Nerve Regeneration: A Tissue-Engineering Approach. The Role of Amnion Tube Nerve Conduit Across a 1-Centermeter Nerve Gap," *Plastic and Reconstructive Surgery*, 105(2): 660-666 (2000).
Nakamura, T., et al., Experimental Study on the Regeneration of Peripheral Nerve Gaps Through a Polyglycolic Acid-collagen (PGA-collagen) Tube, *Brain Research*, 1027: 18-29 (2004).
Navissano, M., et al., "Neurotube® for Facial Nerve Repair," *Microsurgery*, 25: 268-271 (2005).
Scharpf, J., et al., "A Novel Technique for Peripheral Nerve Repair," *The Laryngoscope*, 113: 95-101 (2003).
Scharpf, J., et al., "Immunomodulation with Anit-αβ T-Cell Receptor Monoclonal Antibodies in Combination with Cyclosporine A Improves Regeneration in Nerve Allografts," *Microsurgery*, 26: 599-607 (2006).

(56) References Cited

OTHER PUBLICATIONS

Seckel, B.R., et al., "Nerve Regeneration Through Synthetic Biodegradable Nerve Guides: Regulation by the Target Organ," *Plastic and Reconstructive Surgery*, 74(2): 173-181 (1984).
Siemionow, M. and Sari, A., "A Contemporary Overview of Peripheral Nerve Research from the Cleveland Clinic Microsurgery Laboratory," *Neurological Research* 26: 218-225 (2004).
Siemionow, M. and Brzezicki, G., "Current Techniques and Concepts in Peripheral Nerve Repair," *International Review of Neruobiology*, 87:141-172 (2009).
Siemionow, M., et al., "Epinerual Sleeve Neurorrhaphy: Surgical Technique and Functional Results—A Preliminary Report," *Annals of Plastic Surgery*, 48(3): 281-285 (2002).
Siemionow, M. and Sonmez, E., "Nerve Allograft Transplantation: A Review," *Journal of Reconstructive Microsurgery*, 23(8): 511-520 (2007).
Siemionow, M., et al., "Repair of Peripheral Nerve Defects with Epineural Sheath Grafts," *Annals of Plastic Surgery*, 65(6): 546-554 (2010).
Siemionow, M., et al., "The Single-Fascicle Method of Nerve Grafting," *Annals of Plastic Surgery*, 52(1): 72-79 (2004).
Snyder, C.C., "Epineurial Repair," *The Orthopedic Clinics of North America*, 12(2) 267-276 (1981).
Tang, J., "Vein Conduits with Interposition of Nerve Tissue for Peripheral Nerve Defects," *Journal of Reconstructive Microsurgery*, 11(1): 21-26 (1995).
Tetik, C., et al., Conventional Versus Epineural Sleeve Neurorrhaphy Technique: Functional and Histomorphometric Analysis, *Annals of Plastic Surgery*, 49(4): 397-403 (2002).
Watchmaker, G.P. and Mackinnon, S.E., "Advances in Peripheral Nerve Repair," *Clinics in Plastic Surgery*, 24(1): 63-73 (1997).
Weber, R.A., et al., "A Randomized Prospective Study of Polyglycolic Acid Conduits for Digital Nerve Reconstruction in Humans," *Plastic and Reconstructive Surgery*, 106(5): 1036-1045 (2000).
Yavuzer, R., et al., "Turnover Epineural Sheath Tube in Primary Repair of Peripheral Nerves," *Annals of Plastic Surgery*, 48(4): 392-400 (2002).
Zamboni, W.A., et al., "Functional Evaluation of Peripheral-Nerve Repair and the Effect of Hyperbaric Oxygen," *Journal of Reconstructive Microsurgery*, 11(1): 27-30 (1995).
Jul. 27, 2009, Notification of Transmittal of the International Search Report and the Written Opinion of the International Search Authority, or the Declaration, PCT/US2009/039258.
Duggan, W., et al., "Transplanted Donor Derived Bone Marrow Stromal Cells Engraft Locally and Systemically When Augmenting the Regeneration of Peripheral Nerve Defects", *The 2009 Annual Meeting of OASYS_NEW*, Jan. 11, 2009.
Goel, R.K., et al., "Effect of Bone Marro-Derived Mononuclear Cells on Nerve Regeneration in the Transection Model of the Rat Sciatic Nerve", *Journal of Clinical Neuroscience*, 16: 1211-1217 (2009).

Siemionow, M., et al., "Peripheral Nerve Defect Repair With Epineural Tubes Supported With Bone Marrow Stromal Cells: A Preliminary Report", *Annals of Plastic Surgery*, 67(1): 73-84 (2011).
Oct. 22, 2010, Notification of Transmittal of the International Search Report and the Written Opinion of the International Searching Authority, PCT/US2010/047547 Methods of Engineering Neural Tissue.
Mar. 6, 2012, International Preliminary Report on Patentability, PCT/US2010/047547 Methods of Engineering Neural Tissue.
Sigma-Aldrich Cell Culture, Dulbecco's Modified Eagle's Medium (DME) Formulation; downloaded Mar. 8, 2014 from URL: http://www.sigmaaldrich.com/life-science/cell-culture/learningcenter/media-formulations/dme.printerview.html.
Chen, Chun-Jung, et al., "Transplantation of Bone Marrow Stromal Cells for Peripheral Nerve Repair," *Exp. Neuro.*, 204: 443-453 (2007).
Communication pursuant to Article 94(3), Examination Report for EP 10814436.1; "Methods of Engineering Neural Tissue", dated Dec. 2, 2014.
Ignatiadis, I.A., et al., "Diverse Types of Epineural Conduits for Bridging Short Nerve Defects. AnExperimental Study in the Rabbit," *Microsurgery*, 27: 98-104 (2007).
Rodriguez, F. J., et al., "Nerve Guides Seeded with Autologous Schwann Cells Improve Nerve Regeneration," *Exp. Neuro.*, 161: 571-584 (2000).
Communication pursuant to Article 94(3), Examination Report for EP 108144361, "Methods of Engineering Neural Tissue," dated Dec. 2, 2014.
Supplementary European Search Report for EP 108144361, "Methods of Engineering Neural Tissue"; dated Apr. 4, 2013.
Communication pursuant to Article 94(3) EPC, Examination Report for EP 108144361, "Methods of Engineering Neural Tissue"; dated Nov. 25, 2013.
Karacaoğlu, E., et al., "Nerve Regeneration Through an Epineurial Sheath: Its Functional Aspect Compared With Nerve and Vein Grafts", *Microcurgery*, 21: 196-201 (2001).
Communication Pursuant to Article 94(3) EPC, Examination Report for EP Application No. 10814436.1, "Methods of Engineering Neural Tissue," dated Jul. 13, 2015.
Office Action, U.S. Appl. No. 13/393,750, "Methods of Engineering Neural Tissue," dated Mar. 18, 2015.
Office Action, U.S. Appl. No. 13/393,750, "Methods of Engineering Neural Tissue," dated Jan. 15, 2015.
Communication pursuant to Article 94(3), Examination Report for EP 10814436.1; "Methods of Engineering Neural Tissue", dated Feb. 3, 2016.
Communications pursuant to Article 94(3), Examination Report for EP 10814436.1 "Methods of Engineering Neural Tissue", dated Dec. 2, 2014.
Communicatijon pursuant to Article 94(3), Examination Report for EP 10814436.1: "Methods of Engineering Neural Tissue", dated Jul. 7, 2016.

* cited by examiner

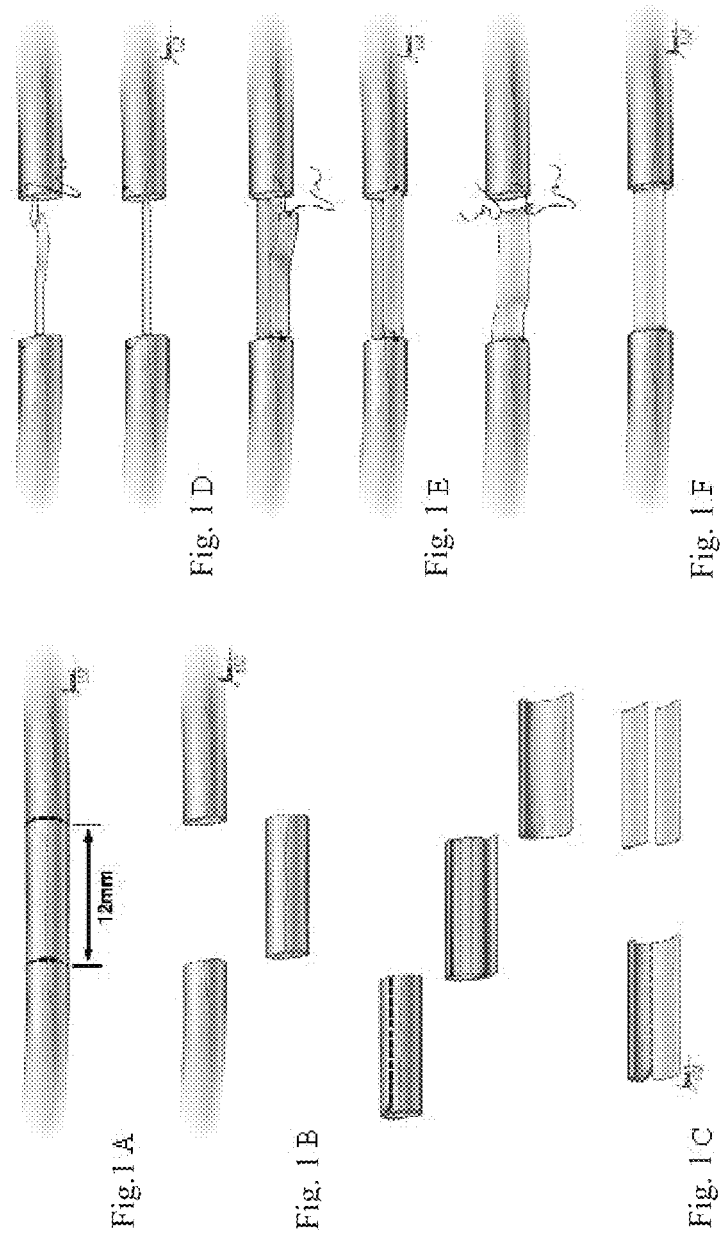

Fig. 2A
Fig. 2B
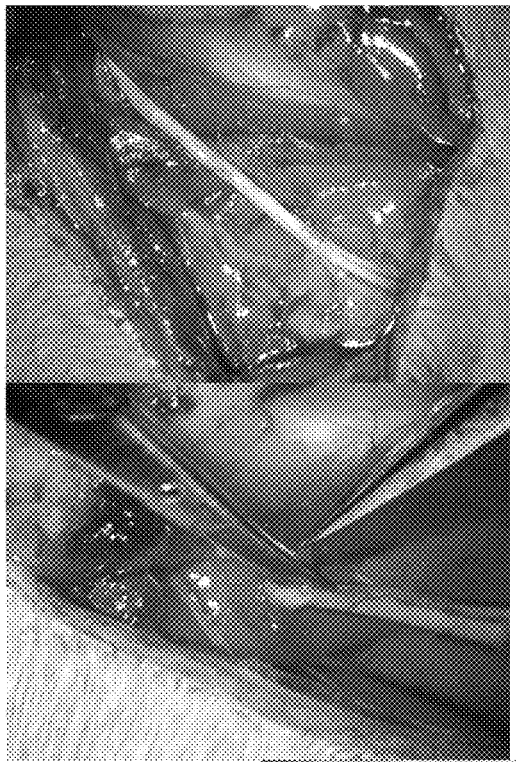
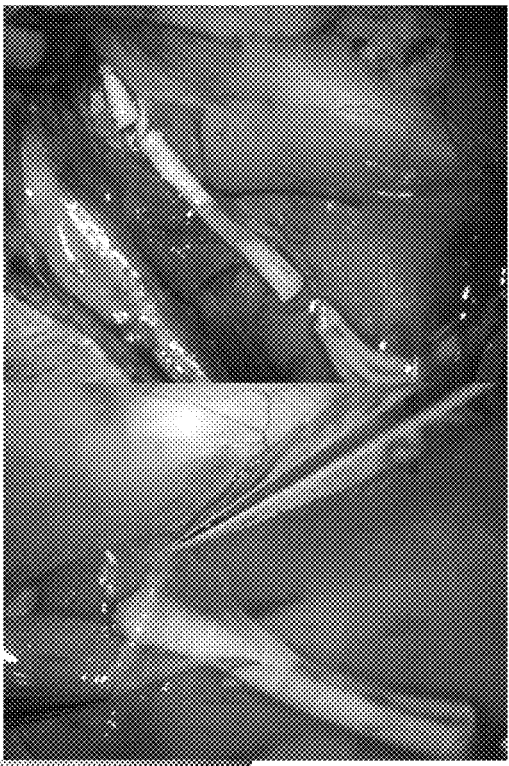
Fig. 2C
Fig. 2D
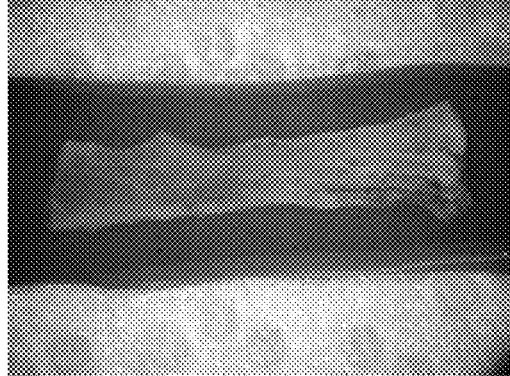
Fig. 2E

Harvesting the Epineural Tubes
Fascicles are taken out of the 15 mm fragment A. straight irrigator - 30ga x 1" (25 mm) with saline
B. Fascicles taken out
C. Ready to transplant epineural tube Harvesting the Epineural Tubes
Injection of Stromal Cells
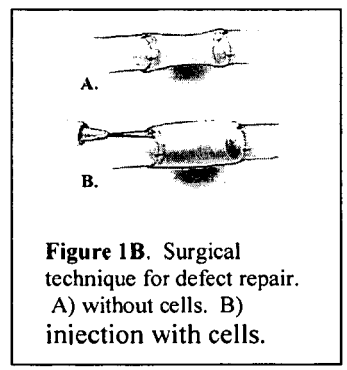
BMSCs therapy (2.5-3.0 X $10^6$) delivered directly into transplanted epineural tube
Bone Marrow Stromal Cells (BMSC) Preparation
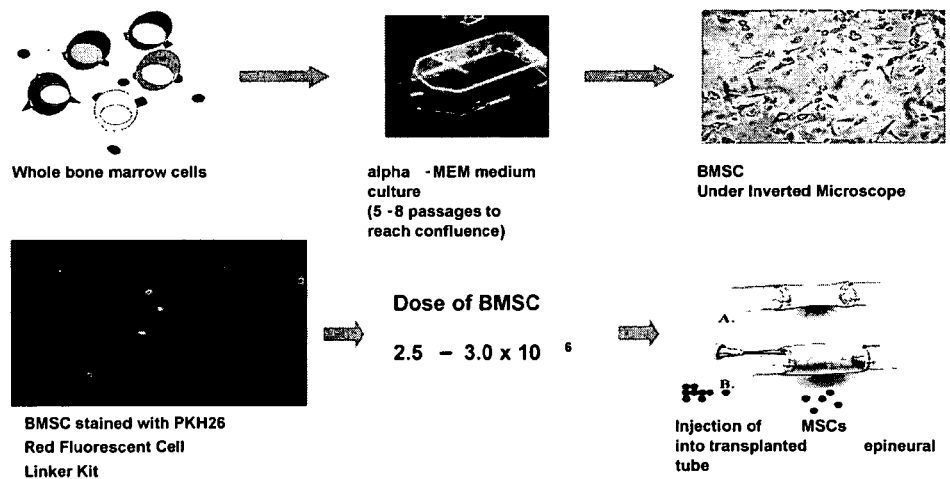
Fig. 12

Histology 12 weeks after Rat Sciatic Nerve repair. A) Saline Injection, B) Isogenic BMSCs, C) Allogenic BMSCs. Isogenic BMSCs showed higher number of regenerated axons (90.6 ± 26.9) compared to Group A (71.4 ± 3.0) and Group C (76.4 ± 5.4)

Pump Operated Nerve Harvesting System
Epinural Tube Recovery Device

1. Nerve Harvesting Cannula
2. Rotatory Nerve Harvesting Drive
3. Flexible Irrigation Pipe
4. Irrigating Pump System

USE OF EPINEURAL SHEATH GRAFTS FOR NEURAL REGENERATION AND PROTECTION

RELATED APPLICATION(S)

This application is the U.S. National Stage of International Application No. PCT/US2009/039258, filed Apr. 2, 2009, which designates the U.S., published in English, and claims the benefit of U.S. Provisional Application No. 61/123,026, filed on Apr. 4, 2008. The entire teachings of the above application(s) are incorporated herein by reference.

BACKGROUND OF THE INVENTION

Severe nerve injuries may result in significant gaps and surgical management of nerve defects is still a major challenge. When direct repair of the injured nerve with epineural sutures is impossible, the defect between the nerve stumps has to be bridged by a conduit of some kind, which will facilitate axonal regeneration towards the distal nerve stump. Currently, the microsurgical techniques used for the repair of peripheral nerve defects do not always result in optimal functional outcome. The most reliable and widely used method is bridging the defect by an autograft, which is considered the gold standard for nerve gap repair (Watchmaker, G P et al., *Clin. Plast. Surg,* 24:63-73 (1997); Siemionow, M., et al., *Ann. Plast. Surg.,* 52:72-79 (2004)). Autografts can be obtained from functionally less important cutaneous sensory nerves such as a sural nerve, medial antebrachial cutaneous nerve, saphenous nerve, superficial radial nerve and lateral antebrachial cutaneous nerve, which are associated with some donor site morbidity such as scarring, anesthesia, neuroma formation (Brandt, J., et al., *J. Hand Surg. [Br],* 24:284-290 (1999); MacKinnon, S E, *Ann. Plast. Surg.,* 22:257-273 (1989)). There is also a limited source of donor nerves available that makes reconstruction of large nerve defects difficult. Nerve allografts have been studied experimentally and used clinically, however the major disadvantage is the need for immunosuppression to prevent rejection (Mackinnon, S E., *Plast. Reconstr. Surg.* 107:1419-1429 (2001); Fox, I K, *Muscle Nerve,* 31:59-69 (2005)). Therefore nerve allografts are used only in selected cases and are not the primary choice of peripheral nerve repair in clinical practice.

Various natural and synthetic conduit materials have been investigated as an alternative technique to nerve autografts. Vein grafts, collagen, muscle, denatured muscle basal lamina, tendon, mesothelium, amnion and epineural sheaths are the natural conduits investigated by researchers (Tang, J B, *J. Reconstr. Microsurg.,* 11:21-26 (1995); Mohammad, J., *Plast. Reconstr. Surg.,* 105:660-666 (2000); Chen, L E, *J. Reconstr. Surg.,* 10:137-144 (1994); Atabay, K., et al., *Plast. Surg. Forum,* 18:121 (1995); Siemionow, M., et al., *Ann. Plast. Surg.,* 48:281-285 (2002); Tetik, C., et al., *Ann. Plast. Surg.,* 49:397-403 (2002); Ayhan, S., et al., *J. Reconstr. Microsurg.,* 16:371-378 (2000); Yavuzer, R., et al., *Ann Plast. Surg.,* 48:392-400 (2002); Lundborg, G., et al., *J Hand Surg. [Am],* 7:580-587 (1982); Archibald, S J., et al., *J. Comp. Neurol.,* 306:685-696 (1991); Keskin, M., et al., *Plast, Reconstr. Surg.,* 113:1372-1379 (2004)). Synthetic materials for bridging the defect have gained attention and silicon tubes, polylactic acid, polyglycolic acid, poly-3-hydroxybutyrate, polyurethane, and poly(organo)phosphazene tubes were used in experimental and clinical studies with encouraging results (Hudson, T W, et al., *Clin. plast. Surg.,* 26:485-497 (1999); Langone, F., et al., *Biomaterails,* 16:347-353 (1995); Lundborg, G., et al., *Exp. Neurol.,* 76:361-375 (1982); Weber, R A., et al., *Plast. Reconstr. Surg,* 106:1036-1045 (2000); Hazari, A., et. al., *Br. J. Plast. Surg.,* 52:653-657 (1999); Navissano, M., et al., *Micorsurgery,* 25:268-271 (2005); Nalamura, T., et al., *Brain Res.,* 1027:18-29 (2004)). These conduits are used as tubulized chambers and present with different advantages, but also disadvantages such as inflammation, foreign body reaction, compression, and toxicity of degradation products.

Alternative methods and compositions with less morbidity for treating nerve injuries are needed.

SUMMARY OF THE INVENTION

Described herein is conduit material that causes minimal inflammatory reaction, and can serve as a structural guide for regenerating, or as a shield for protecting, nerve tissue (e.g., axons). Thus, the invention is directed to methods of treating an injury to a (one or more) nerve or protecting a nerve in an individual in need thereof. The methods employ all or a portion of an isolated, naturally occurring epineural sheath, and can be used, for example, to regenerate nerve tissue in an individual in need thereof.

In one embodiment, the invention is directed to a method of repairing a nerve gap having a proximal nerve stump and a distal nerve stump in an individual in need thereof. The method comprises attaching all or a portion of an (one or more) isolated, naturally occurring epineural sheath (e.g., in the form of a tube, a flat sheath, a strip, a patch, a cord, a scaffold, a paste or a powder) to the proximal nerve stump and to the distal nerve stump, thereby producing a nerve graft. The nerve graft is maintained under conditions in which nerve tissue is regenerated between the proximal nerve stump and the distal nerve stump, thereby repairing the nerve gap.

In a particular embodiment, the invention is directed to a method of repairing a nerve gap having a proximal nerve stump and a distal nerve stump in an individual in need thereof, comprising attaching an isolated, naturally occurring epineural tube to the proximal nerve stump and to the distal nerve stump, thereby producing a nerve graft. The nerve graft is maintained under conditions in which nerve tissue is regenerated between the proximal nerve stump and the distal nerve stump, thereby repairing the nerve gap.

In a particular embodiment, the invention is directed to a method of repairing a nerve gap having a proximal nerve stump and a distal nerve stump in an individual in need thereof, comprising attaching a flat epineural sheath (e.g., a full rectangular epineural sheath) to the proximal nerve stump and to the distal nerve stump, thereby producing a nerve graft. The nerve graft is maintained under conditions in which nerve tissue is regenerated between the proximal nerve stump and the distal nerve stump, thereby repairing the nerve gap.

In another embodiment, the invention is directed to a method of repairing a nerve gap having a proximal nerve stump and a distal nerve stump in an individual in need thereof, comprising attaching at least one epineural strip (a first epineural strip, a second epineural strip, a third epineural strip, a fourth epineural strip, etc.) to the proximal nerve stump and to the distal nerve stump, thereby producing a nerve graft. The nerve graft is maintained under conditions in which nerve tissue is regenerated between the proximal nerve stump and the distal nerve stump, thereby repairing the nerve gap. The method can further comprise splitting an epineural sheath longitudinally, thereby producing a first epineural strip, a second epineural strip, a third epineural strip, etc. prior to attaching the first epineural strip, the second epineural strip, the third epineural strip, the fourth epineural strip etc. to the nerve stump.

In a particular embodiment, the invention is directed to a method of repairing a nerve gap having a proximal nerve stump and a distal nerve stump in an individual in need thereof, comprising attaching a first epineural strip to the proximal nerve stump and to the distal nerve stump, and attaching a second epineural strip to the proximal nerve stump and to the distal nerve stump, thereby producing a nerve graft. The nerve graft is maintained under conditions in which nerve tissue is regenerated between the proximal nerve stump and the distal nerve stump, thereby repairing the nerve gap. The method can further comprise splitting an epineural sheath longitudinally, thereby producing a first epineural strip and a second epineural strip, prior to attaching the first epineural strip and the second epineural strip to the nerve stump.

The invention is also directed to a method of protecting neural tissue in an individual in need thereof, comprising attaching an isolated, naturally occurring epineural sheath to the neural tissue (e.g., a dorsal root ganglion, spinal cord), thereby covering the neural tissue and maintaining the neural tissue under conditions in which neural tissue is isolated, thereby protecting the neural tissue. In one embodiment, the neural tissue is injured neural tissue. In another embodiment, the injured neural tissue produces neuropathic pain in the individual. In yet another embodiment, the injured neural tissue is compressed. In particular embodiments, the neural regeneration occurs.

A device for harvesting (isolating) an epineural sheath is also provided herein. The device for harvesting an epineural sheath comprises a hollow tube having a distal end and a proximal end, wherein the distal end comprises a forwardly curved protrusion extending from a side wall of the tube and curving radially inward to a central line of the tube, and the proximal end comprises a flange. In one embodiment, the hollow tube is rotatably coupled to a rotating drive. In another embodiment, the device further comprises an irrigation system in fluid communication with the hollow tube. The irrigation system can be in fluid communication with the hollow tube using, for example, flexible tubing.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1F are schematic representations of one embodiment of the methods described herein. The preparation of the rectangular epineural sheath graft (FIGS. 1A, 1B and 1C). Repair of the defect with one strip (FIG. 1D), two-strips (FIG. 1E) and full rectangular epineural sheath graft (FIG. 1F).

FIGS. 2A-2E are photographs showing creation of the nerve defect (FIGS. 2A and 2B). The epineurium is incised with scissor (FIGS. 2C and 2D) and flat rectangular shaped epineural sheath graft is obtained (FIG. 2E).

(FIG. 8B) the vascularization of the nerve at the distal repair site from the distal towards the graft.

(FIG. 9C) Section from graft in group 3 (one-strip) showing paucity of regenerating axons (magnification ×400)

FIG. 12 is a schematic of harvesting of an epineural tube and bone marrow stromal cell (BMSC) preparation.

DETAILED DESCRIPTION OF THE INVENTION

Figures 3A, 3B, 3C:
FIGS. 3A-3C are photographs showing the appearance after the repair of the nerve defect with one-strip (FIG. 3A), two-strip (FIG. 3B) and full rectangular epineural sheath graft (FIG. 3C)

Provided herein are methods of treating a neural injury (e.g., an injury to a peripheral nerve; an injury to a cranial nerve; injury to the spinal cord) in an individual in need thereof. In particular embodiments, the invention provides methods of repairing and/or protecting nerve tissue in an individual in need thereof, comprising attaching all or a portion of an (one or more) isolated, naturally occurring epineural sheath to the nerve tissue in need of repair or protection. In some instances, all or a portion of the (one or more) isolated, naturally occurring epineural sheath is used to repair a nerve (e.g., as a nerve graft to repair a nerve gap). In other instances, all or a portion of the isolated, naturally occurring epineural sheath is used as to cover or shield a neural tissue (e.g., as an epineural patch to cover dura in the brain (e.g., cerebellum); as a nerve patch cover an intact nerve that is damaged). An intact nerve or nerve root can be damaged, for example, due to inflammation such as in the case of laminectomy, after surgical intervention of decompression in diabetic and non-diabetic neuropathies, after neuroma resection, etc.

The nerve graft and/or nerve patch is maintained under conditions in which the nerve tissue is repaired and/or protected. The methods can be used, for example, to regenerate nerve tissue in an individual in need thereof.

In a particular embodiment, the invention provides for a method of repairing a nerve gap having a proximal nerve stump and a distal nerve stump in an individual in need thereof. In the method, an isolated, naturally occurring epineural sheath is attached to the proximal nerve stump and to the distal nerve stump, thereby producing a nerve graft. The nerve graft is maintained under conditions in which nerve tissue is regenerated between the proximal nerve stump and the distal nerve stump, thereby repairing the nerve gap.

Typically, nerve fibers are wrapped in a connective tissue called the endoneurium. Groups of fibers surrounded by their endoneurium are arranged in bundles called fascicles, and each fascicle is wrapped in connective tissue called the perineurium. The outermost covering around the entire nerve is the epineurium. As used herein an (one or more) "epineural sheath" is an (one or more) epineurium of a (one or more) nerve. As described herein, an isolated, naturally occurring epineurium sheath is used in the methods of the invention. A "naturally occurring" epineural sheath refers to an epineural sheath obtained from natural sources; that is, an epineural sheath that is not synthetic (non-synthetic). Epineural sheaths that are "isolated", include pure (essentially pure) epineural sheaths, that have been separated away from molecules and other tissues (e.g., endoneurium, perineurium, fasicles, blood components, inflammatory molecules) of their source of origin (e.g., an individual; an isolated nerve), and include epineural sheaths obtained by methods described herein or other suitable methods.

The epineural sheath can be obtained from a variety of nerves, such as nerves from invertebrates, vertebrates or a combination thereof. In one embodiment, the naturally occurring, isolated epineural sheath is obtained from (isolated from) a mammalian nerve such as a nerve of primate (e.g., human), porcine, canine, feline, bovine, and/or murine origin. In other embodiments, the epinueral sheath is an autologous epineural sheath, an allogenic epineural sheath, an isogenic epineural sheath, a xenogenic epineural sheath or a combination thereof. In a particular embodiment, the epineural sheath is obtained from a cadaver (e.g., a human cadaver).

In addition, the epineural sheath can be obtained from a variety of type of nerves, such as from a sensory nerve and/or a motor nerve. For example, although not necessary, in embodiments in which the methods are used to repair a nerve gap in a sensory nerve, the epineural sheath can be obtained from a sensory nerve (e.g., from a sensory nerve that is the same as, similar to or different from, the sensory nerve that is being repaired); and in embodiments in which the methods are used to repair a nerve gap in a motor nerve, the epineural sheath is obtained from a motor nerve (e.g., from a motor nerve that is the same as, similar to or different from, the motor nerve that is being repaired).

As will be apparent to one of skill in the art, all or a portion of an naturally occurring, isolated epineural sheath can take a variety of shapes for use in the methods of the invention, and the shape will depend upon a variety of factors, such as the properties of the nerve that is to be repaired (e.g., nerve type, nerve diameter, nerve length), the type of nerve injury and/or the condition of the individual (e.g., patient). For example, one or more epineural sheaths can be used as a tube (e.g., a tube having two free ends or lumens; a hollow tube), or one or more tubes can be longitudinally split and used as a flat rectangular sheath. In addition, one or more epineural sheaths can be formed into one or more strips, cords (e.g., twisted strips, plain or enriched with cells), patches, scaffolds (e.g., filled with cells, slow-releasing growth factor), pastes, powders (e.g., with a gel), putty(ies) or a combination thereof for use in the methods of the invention. As will be apparent to one of skill in the art, one or more of these forms can be achieved using one or more epineural sheaths (e.g., multiple epineural sheaths secured together, e.g., as a large sheet or secured together in multiple layers and filled with powder, gel and/or factors that enhance nerve growth and/or regeneration).

In the methods of the invention, all or a portion of a naturally occurring, isolated epineural tube can be used. In one embodiment, one or more naturally occurring, isolated epineural tubes can be used in the methods. In another embodiment, one or more naturally occurring, isolated epineural tubes can be split (e.g., longitudinally) and used as a (e.g., flat) rectangular sheath in the methods. In embodiments in which two or more naturally occurring, isolated epineural tubes are split longitudinally thereby producing two or more rectangular sheaths, the two or more rectangular sheaths can be used to make a large rectangular sheath or placed in layers. In yet another embodiment, the epineural tube can be split (e.g., longitudinally) into one or more strips, and the epineural strips can be used in the methods described herein.

Accordingly, the invention is directed to a method of repairing a nerve gap having a proximal nerve stump and a distal nerve stump in an individual in need thereof, comprising attaching an isolated, naturally occurring epineural tube to the proximal nerve stump and to the distal nerve stump, thereby producing a nerve graft (e.g., a tubular nerve graft). The nerve graft is maintained under conditions in which nerve tissue is regenerated between the proximal nerve stump and the distal nerve stump, thereby repairing the nerve gap In another embodiment, the invention is directed to method of repairing a nerve gap having a proximal nerve stump and a distal nerve stump in an individual in need thereof, comprising attaching a flat epineural sheath to the proximal nerve stump and to the distal nerve stump, thereby producing a nerve graft. The nerve graft is maintained under conditions in which nerve tissue is regenerated between the proximal nerve stump and the distal nerve stump, thereby repairing the nerve gap.

In yet another embodiment, the invention is directed to a method of repairing a nerve gap having a proximal nerve stump and a distal nerve stump in an individual in need thereof, comprising attaching at least one epineural strip (multiple strips, such as a first epineural strip, a second epineural strip, a third epineural strip, a fourth epineural strip, etc.) to the proximal nerve stump and to the distal nerve stump, thereby producing a nerve graft. The nerve graft is maintained under conditions in which nerve tissue is regenerated between the proximal nerve stump and the distal nerve stump, thereby repairing the nerve gap.

The method can further comprise splitting an epineural sheath longitudinally, thereby producing one or more epineural strips (multiple strips, such as a first epineural strip, a second epineural strip, a third epineural strip, etc.) prior to attaching the one or more epineural strips to the nerve stump. For example, the method can further comprise splitting an epineural tube longitudinally into a first epineural strip and a second epineural strip, prior to attaching the first epineural strip and the second epineural strip to the nerve stump.

In a particular embodiment, the invention is directed to a method of repairing a nerve gap having a proximal nerve stump and a distal nerve stump in an individual in need thereof, comprising attaching a first epineural strip to the proximal nerve stump and to the distal nerve stump, and attaching a second epineural strip to the proximal nerve stump and to the distal nerve stump, thereby producing a nerve graft. The nerve graft is maintained under conditions in which nerve tissue is regenerated between the proximal nerve stump and the distal nerve stump, thereby repairing the nerve gap.

In particular embodiments of the invention, the length of the defect between the proximal and distal nerve stump is assessed. The epineural sheath (e.g., an epineural tube segment) will match the size of the defect (e.g., about 1, 2, 3, 4, 5, 6, 7, 8, 9, 10, 11, 12, 13, 14, 15, 16, 17, 18, 19, 20 cm of length) between the proximal and distal nerve stump, and the diameter of the proximal and distal nerve stump (e.g., 1, 2, 3, 5, 10, 15, 20, 25, 30 mm of diameter). In particular embodiments, the epineural sheath can match the type of nerve to which it will be connected, which can be either purely sensory (e.g., sural nerve), purely motor (e.g. radial nerve), or mixed sensorimotor nerve type (e.g., median nerve). In these embodiments, the sensory tube will connect the sensory nerve stumps, motor tube, motor nerve stumps, and sensorimotor stumps.

In one embodiment, the epineural tube is connected to the proximal (or distal) nerve stump using microsurgical technique with microsurgical sutures (4-6 sutures 10/0) or using gluing technique with application of different types of tissue sealants or glues, or using staple technique, or a combination of the above. The epineural sheath can be overlying, from about 1 mm to 20 mm, about 3 mm to about 15 mm, about 5 mm to about 10 mm, and about 7 mm to about 12 mm the proximal (or distal) nerve stump, so that the severed proximal (or distal) end of the nerve will be inserted inside the tube. Once the proximal end repair is finished, the same steps will be followed at the distal (or proximal) nerve end by inserting the distal nerve stump into the distal tube segment. The tube can be applied for nerve repair, depending on the length of the gap and nerve diameter. It can be applied as an empty tube to replace existing technologies for short gaps, and in particular, as a tube filled with the different types of cells (e.g., Schwann cells, bone marrow cells, mesenchymal stem cells, chimeric cells), or as a tube filled with nerve growth enhancing factors (e.g., VEGF, NGF growth factor), anti-inflammatory factors, or combination thereof.

The epineural sheath can be used as a patch for a variety of applications. For example, the patch can be used to close dural defects in one of several ways. As a nerve-like and nerve-friendly tissue patch, it can protect neural tissues from inflammatory factors (e.g., cytokines and chemokines) released by the surrounding environment, and keep neural tissue friendly factors accessible via a natural system of nerve-blood barrier or blood-brain barrier.

Accordingly, the invention is also directed to a method of protecting neural tissue in an individual in need thereof, comprising attaching an isolated, naturally occurring epineural sheath to the neural tissue (e.g., a dorsal root ganglion), thereby covering the neural tissue and maintaining the neural tissue under conditions in which the neural tissue is isolated, thereby protecting the neural tissue. In one embodiment, the neural tissue is injured neural tissue. In another embodiment, the injured neural tissue produces neuropathic pain in the individual. In yet another embodiment, the injured neural tissue is compressed. In particular embodiments, neural regeneration occurs.

Using standard surgical technique, an epineural patch of sufficient size (e.g., ranging from 1×1 cm up to 10×10 cm), and thickness (single versus multiple layer patch) which effectively covers and seals off the defect can be secured (e.g., using suture) into the desired position. The effectiveness of the seal can be augmented with various commercially available glues, such as fibrin glue, staplers, and other adhesive materials. Alternatively, the epineural patch can be placed topically as an "on lay graft" on the exposed dura relying on mechanical, chemical or electrostatic adhesive forces to prevent dislodgment, or can be placed topically on the exposed dura and secured with commercially available glue, such as fibrin glue. The epineural patch can be fashioned in such a manner where part or all of the down side is covered with an adhesive substance, such as fibrin glue. It can then placed topically on the exposed neural tissues and secured to the underlying neural tissues by the adhesive properties of the glue. This application can be augmented with BMSCs or MSCs as an inherent part of the graft or BMSCs or MSC's injected under patch surface or between patch layers.

The patch can be also be used to cover exposed neural tissues in one of several ways. In this embodiment, the epineural patch is used as a shielding neuro-like or neuro-friendly tissue which protects injured, decompressed or repaired nerves from forming adhesions with or scarring by non-neural type of tissues in the surroundings such as muscles, bone, tendon, skin. This embodiment helps with nerve gliding after surgery, and protects against nerve exposure to scar tissue formation from underlying or overlying tissues. In this embodiment, the epineural patch protects nerves from becoming adherent to the surrounding non-neural tissues which prevents nerve from development of nerve traction (against adhesion or scar) injury.

The epineural patch can be used as single or multiple layer patch, and can be placed topically on the exposed neural tissues relying on mechanical, chemical or electroadhesive forces to prevent dislodgment. The epineural patch can be placed topically on the exposed neural tissues and secured with commercially available sutures, staplers and glue, such as fibrin glue. The epineural patch can be fashioned in such a manner where part or all of the down side is covered with an adhesive substance, such as fibrin glue. It is then placed topically on the exposed neural tissues and secured to the underlying neural tissues by the adhesive properties of the glue or by sutures.

The above applications can be augmented with bone marrow stromal cells (BMSCs) being the inherent part of the graft or BMSCs injected under patch surface or between patch layers for enhancement of nerve regeneration.

The epineural sheath can also used to inhibit neuroma formation after neuroma revision surgeries requiring nerve implantation into the muscle or bone tissue. The epineural sheath can also be used to cover the transected nerve end (after neuroma resection) by inserting the proximal nerve segment into the proximal end of an epineural sheath tube and attaching the tube to the nerve stump (e.g., using a suture, stapler, sealant or glue). Care should be taken to leave enough space within the tube for the nerve stump to settle freely in the tube, thus, there should be an excess of the epineural tube at the distal end which will be sealed, ligated, sutured or left open before implantation of the nerve-tube complex into the muscle or bone. Thus, the epineural sheath (e.g., an epineural sheath tube) can be used to cover nerve stump after neuroma resection without implantation into the muscle or bone. The technique of covering the neuroma stump is the same as described above.

Compression of the spinal cord and nerve roots can result in irreversible histological and physiological changes such as intraneural fibrosis, demyelination, and neuronal loss. The epineural sheath can be used as a protective anti-inflammatory sheath or to increase neural regeneration or vascularization in patients undergoing decompression procedures for myelopathy secondary to spondylosis, disc herniation, trauma, tumor, and/or complicated by diabetes. In addition, the epineural sheath can be used as a dura mater substitute in cases of a dural deficit, an iatrogenic durotomy and/or a dural transplant. The epineural sheath can also be used to prevent scarring and adhesions in patients undergoing decompressive procedures of the spinal cord, thecal sac, and nerve roots and/or suffering from radiculopathy/myelopathy. The epineural sheath can also be used to increase neuronal regeneration and decrease inflammation in patients with radiculopathy/myelopathy and to create an optimal microenvironment and increase neuronal regeneration in patients suffering from spinal cord injury.

As is apparent to one of skill in the art, different lengths and diameters of epineural sheaths may be used in the methods of the invention, and will depend upon a variety of factors, such as the properties of the nerve that is to be repaired (e.g., nerve type, nerve diameter), the type of neural injury (e.g., the dimensions, such as length and width, of a nerve gap) and/or the condition of the individual. In some embodiments, the epineural sheath can be from about 1 mm to about 10 cm in length. In other embodiments, the epineural sheath can be from about 1 cm to about 10 cm in width. For example, the epineural sheath can have different tube diameters (e.g., about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm) and lengths (e.g., about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm), and patch sizes (about 1 $cm^2 \times 100$ $cm^2$ such as 2×2 cm, 3×3 cm, 4×4 cm, 5×5 cm, 6×6 cm 7×7 cm, 8×8 cm, 9×9 cm, 10×10 cm, 20×20 cm, 30×30 cm, 40×40 cm, 50×50 cm, 60×60 cm, 70×70 cm, 80×80 cm, 90×90 cm, 100 cm×100 cm, etc). The tubes and patches can be linked or custom designed (cut from whole sheath etc.).

Methods for obtaining or harvesting isolated, naturally occurring epineural sheaths are provided herein, and are known to those of skill in the art. In addition, preservation methods to reduce immunogenicity for allografts and to keep stored epineural grafts for off shelf use and banking following methods are also provided herein. After harvesting, cryopreserved, cold stored, or lyophilized epineural sheaths can be used as different lengths, sizes, and widths.

Examples of methods for harvesting an isolated, naturally occurring epineural sheath from the sciatic nerve are provided herein. As will be apparent to one of skill in the art, other methods can be used to harvesting an isolated, naturally occurring epineural sheath from other sources using routine skills. In one embodiment, the access to the peripheral nerve (e.g., sciatic nerve) is made by skin incision and subcutaneous tissue dissection down to the anatomical location of the nerve. At this level the sciatic nerve is cleared of all surrounding tissues by blunt dissection as far proximally as the sacral plexus and as far distally as its division into the terminal nerve branches. All collateral branches arising from the sciatic nerve throughout its length can be detached and used separately to create an epineurial sheath tubular grafts of different size diameters and lengths.

At this point the sciatic nerve is ready to be dissected out. The nerve is transected as proximal as is feasible at its origin from the sacral plexus, and then transected distally where the nerve divides into its terminal components, at the level of insertion into the muscle.

Depending upon the area of nerve harvest, the nerve can then be suspended on either a straight driver/irrigator with round tip (e.g., 30 gauge×25 mm depending on nerve diameter—the driver diameter is typically smaller than nerve diameter), on a curved/hook finished driver/irrigator, or on a screwdriver type of irrigator. The irrigator can be filled with chilled solution (either cryopreservation solution for long term storage, or nerve culture medium or combination of both—depending on the fate of graft) and kept moist on the dissection board by soaking it with 0.9% sodium chloride.

Under microscope or loop magnification the axons can then gently be teased from its epineural sheath with the use of circular motion of driver/irrigator and jeweler fine forceps pulling the sheath away from the axons and driver in the "devaginating maneuver", so that the axon fibers are pulled from the distal end whilst the epineural sheath is held from the proximal end on the driver/irrigator. Once all axons, the perineurium and the endoneurium are removed the intact, clear epineural sheath can be irrigated and left as a product of this process and is then inspected for integrity.

Figure 18:
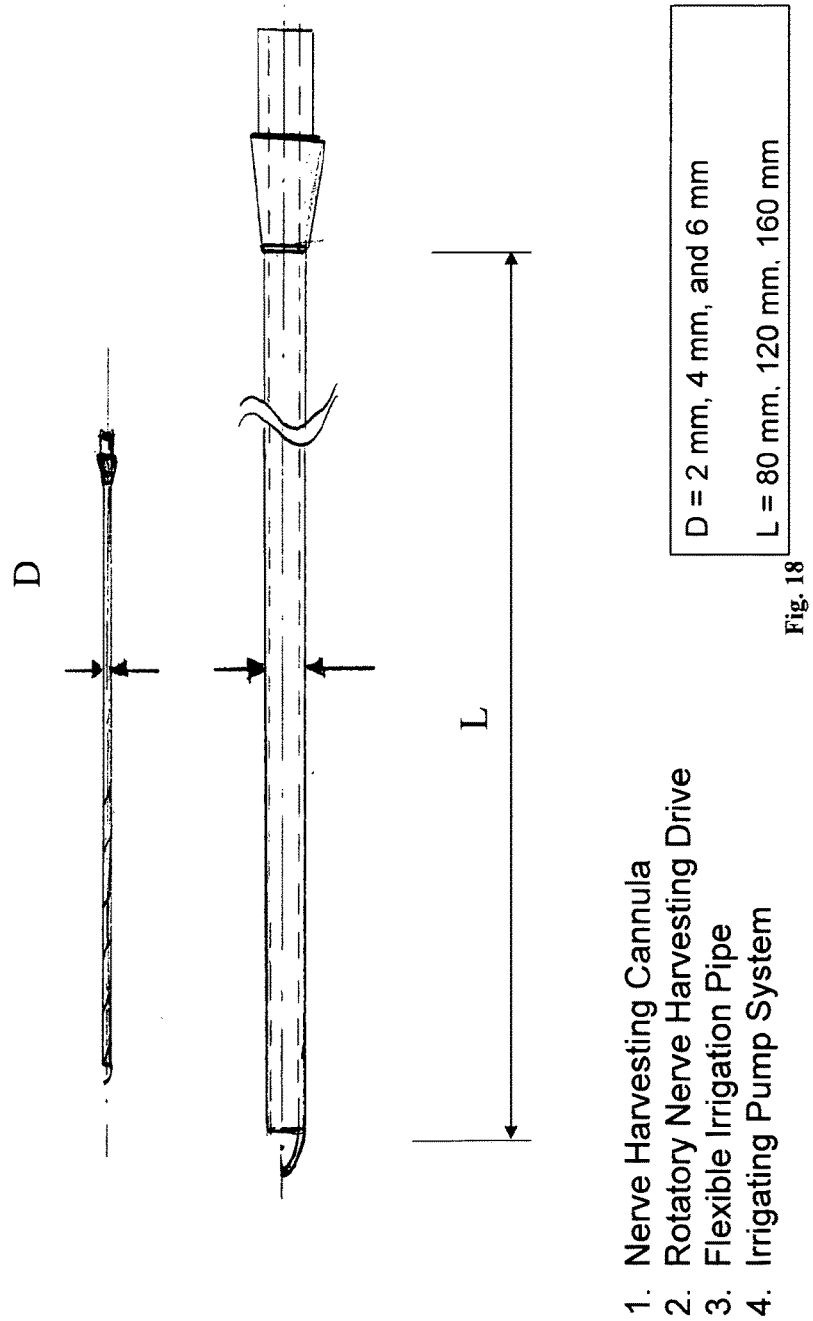
FIG. 18 shows an epineural sheath harvesting device that can be used with a pump operated nerve harvesting system.
Figure 19:
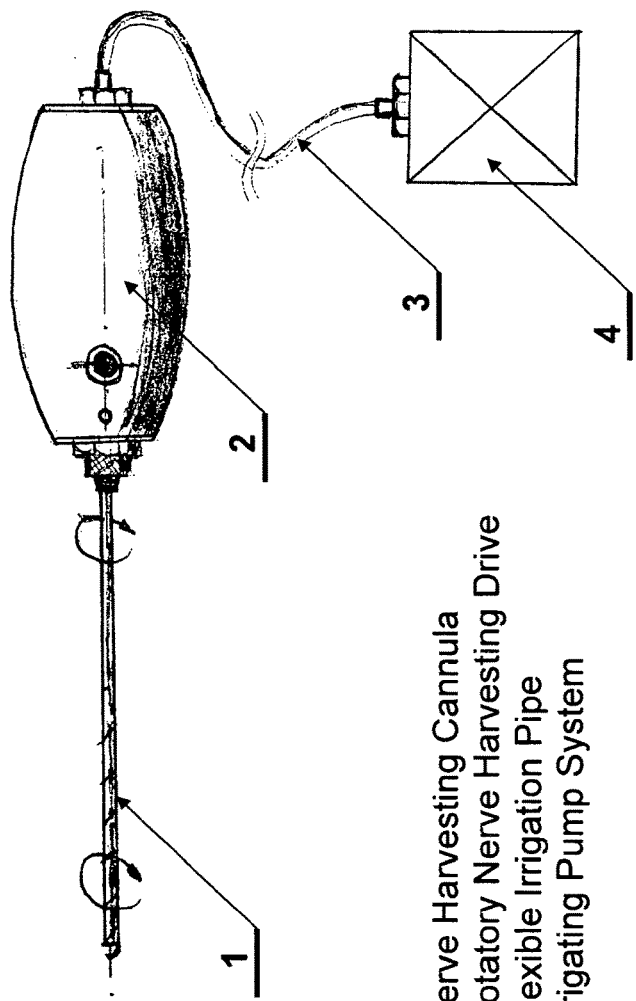
FIG. 19 shows a pump operated epineural sheath harvesting system for use as an epineural tube recovery device.

Accordingly, also provided herein is a device for harvesting (isolating) an epineural sheath (e.g., a device for removing neural tissue (e.g., fascicles, axons) from its epineurium, thereby harvesting an epineural tube). Example of such a device are provided in FIGS. 18 and 19.

In one embodiment, the device for harvesting an epineural sheath comprises a hollow tube having a distal end and a proximal end, wherein the distal end comprises a forwardly curved protrusion extending from a side wall of the tube and curving radially inward (forward) to a central line of the tube, and the proximal end comprises a flange (e.g., shoulder). Any type of hollow tube, such as a hollow needle, a hollow catheter, and a hollow cannula, can be used in the device provided herein. The length and diameter of the hollow tube will depend upon the type of nerve from which the epineural sheath is being harvested. For example, the hollow tube can range in diameter from about 0.1 mm to about 15 mm. In particular embodiments, the diameter of the hollow tube is about 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, 11 mm, 12 mm, 13 mm, 14 mm, or 15 mm. The hollow tube can range in length from about 50 mm to about 180 mm. In particular embodiments, the length of hollow tube is about 50 mm, 55 mm, 60 mm, 65 mm, 70 mm, 75 mm, 80 mm, 85 mm, 90 mm, 95 mm, 100 mm, 105 mm, 110 mm, 115 mm, 120 mm, 125 mm, 130 mm, 135 mm, 140 mm, 145 mm, 150 mm, 155 mm, 160 mm, 165 mm, 170 mm, 175 mm, or 180 mm.

The curved protrusion (e.g., tip, hook, prong, anchor) at the distal end of the hollow tube is used to engage (e.g., capture, grab) the nerve fiber(s) within the epineural sheath. Depending on the type of nerve within the epineural sheath that is to be removed (e.g., extracted), the protrusion can be thin, wide, flat, rounded or some combination thereof.

The flange at the distal end of the hollow tube is present to provide, for example, increased thickness and/or strength to the hollow tube. In addition the flange can be used to attach additional components to the device.

For example, the hollow tube can be rotatably coupled to a rotating drive, such as a drill or a pump.

The device can also comprise an irrigation system that is in fluid communication with the hollow tube. In one embodiment, the irrigation system is an irrigation pump. The irrigation system can be in fluid communication with the hollow tube using, for example, flexible tubing.

In a particular embodiment, the device for harvesting an epineural sheath comprises (a) a hollow tube having a distal end and a proximal end, wherein the distal end comprises a forwardly curved protrusion extending from a side wall of the tube and curving radially inward to a central line of the tube, and the proximal end comprises a flange, (b) a rotating device that is rotatably coupled to the flange of the hollow tube, and (c) an irrigation system that is attached to the rotating device and which is in fluid communication with the hollow tube.

As will be apparent to those of skill in the art, the device can be portable or stationary. As will also be apparent the device can be used in combination with other devices or instruments such as forceps to pull the sheath away from the distal end of the device.

Also provided is a method of harvesting (isolating) an epineural sheath using the device as described herein.

Following harvesting of the epineural sheath, the epineural sheaths can be stored for later use. For example, following harvesting, the epineural sheaths can be saturated with dimethlyosulfoxide (cryopreserving agent) and frozen (e.g., by computer controlled freezer (−196 degrees Celcius)) and stored in liquid nitrogen. See Example 3 for more details of this embodiment of the invention.

In one embodiment, an acellular tissue matrix can be fractured so as to give a particulate tissue matrix. The acellular tissue matrix can be made from all or part of cadaver areolar connective tissue with vascular components disposed among randomly and partly longitudinally arranged bundles of collagen fibrils; and can include collagen fibrils and elastic fibers to which, subsequent to rehydration, viable neural cells, endothelial cells, or viable epithelial cells attach. This tissue matrix can be in the form of, for example, a patch of variable shape, variable thickness, variable surface area, which can be either single layered or multilayered, with the option of adding cells or growth factor in-between the layers ("sandwich patch").

In another embodiment, the method comprises fracturing an cellular tissue matrix so as to give a particulate tissue matrix. The cellular tissue matrix can be made from all or part of cadaver areolar connective tissue with vascular components disposed among randomly and partly longitudinally arranged bundles of collagen fibrils; and can include collagen fibrils and elastic fibers to which viable neural cells, endothelial cells, or viable epithelial cells attach. This tissue matrix can be in the form of, for example, a patch of variable shape, variable thickness, variable surface area, which can be either single layered or multilayered, with the option of adding cells or growth factor in-between the layers ("sandwich patch").

As described herein, the methods of the invention provide for methods of repairing and/or protecting nerve tissue in an individual in need thereof. In a particular embodiment, the methods are used to repair a nerve gap. As used herein, a "nerve gap" refers to an interruption (partial, complete) of continuity (e.g., a break, a lesion, traumatic or iatrogenic transaction or resection) in a (one or more) nerve or fascicle, which results in a nerve or fascicle having an interruption (partial, complete) of conduction. In particular embodiments, the nerve gap is from about 0.5 mm to about 20 cm, from about 1 mm to about 18 cm, from about 2 mm to about 16 cm, about 4 mm to about 14 cm about 6 mm to about 12 mm and about 8 mm to about 10 cm. As a result of the nerve gap, a nerve having a proximal nerve stump and a distal nerve stump is produced.

In the methods of the invention, an isolated, naturally occurring epineural sheath is attached to the proximal nerve stump and the distal nerve stump, thereby producing a nerve graft that bridges (spans; connects; links) the proximal nerve stump to the distal nerve stump. The epineural sheath can be attached to the proximal and distal nerve stumps using a variety of methods known to those of skill in the art. For example, the epineural sheath can be attached using one or more sutures, glues (e.g., fibrin glue), staples, other adhesive materials or a combination thereof. In a particular embodiment, the epineural sheath is attached to the proximal nerve stump using at least one suture and attached to the distal nerve stump using at least one suture.

The nerve graft produced is maintained under conditions in which nerve tissue is regenerated and/or nerve conduction (partial or complete) between the proximal nerve stump and the distal nerve stump is regained. For example, as will be apparent to one of skill in the art, in some embodiments, after introducing the nerve graft in an individual as described herein, the area of the nerve graft (e.g., the surgical area) can be maintained under conditions to (in an environment that) promote healing, and prevent or minimize scar formation and/or infection, of the area.

The methods described herein can further comprise contacting the epineural sheath (e.g., filling the graft; coating the sheath) with cells that aid and/or enhance regeneration of neural tissue. Examples of such cells include progenitor cells, stem cells (e.g., mesenchymal stem cells), bone marrow derived cells (e.g., bone marrow stromal cells (BMSC)), mesenchymal stromal cells, dendritic cells, adipose (fat) cells, or a combination thereof (e.g., chimeric cells). The cells can be autologous, allogenic, isogenic, xenogenic or a combination thereof (e.g., chimeric cells). As used herein, a "chimeric cell" refers to a cell which is a fusion of one or more autologous, allogenic, or isogenic cells with one or more autologous, allogenic, or isogenic cells. The fused cells can be the same (e.g., one or more BMSC fused with one or more BMSC), similar (e.g., one or more BMSC fused with one or more mesemchymal stromal cells) or different (e.g., one or more BMSC fused with one or more dendritic cells) type of cell. In a particular embodiment, the chimeric cell is a donor cell (e.g., a donor origin bone marrow progenitor such as a CD90 cell) fused with a recipient cell which is the same type of cell as the donor cell (e.g., a donor origin bone marrow progenitor such as a CD90 cell).

In addition, the methods described herein can further comprise contacting (e.g., filling the graft; coating the sheath) the epineural sheath or nerve graft with factors that aid or enhance regeneration of nerve tissue. Examples of such factors include neurotropic and neurotrophic factors. Specific examples include nerve growth factors (NGF), vascular endothelial growth factor (VEGF), brain derived nerve growth factor (BDNGF), insulin-like nerve growth factor (INGF), glial fibrillary acidic protein (GFAP), laminin B2, cilliary nerve growth factor. In addition, anti-inflammatory agents can be used in the methods of the invention. Examples of such agents include steroids (e.g., DHEA), Kenalog and dexomethason.

The methods of the invention can also comprise contacting the epineural sheath or nerve graft with, or administering to the individual, one or more immunosuppressants, particularly in embodiments in which the epineural sheath is of non-autologous origin. Examples of immunosuppressants or immunosuppressant protocols which can be used include different types of antibodies (e.g., Thymoglobulin, Camptah, Daclizumab, etc.) and alpha/beta TCR/CsA protocol, Cyclosporine A protocol, Tacrolimus, Sirolimus, Rapamycin, Celcept, mycofolenate moefetil, and/or steroids.

In the methods described herein, it will be apparent to one of skill in the art that the factors and/or immunosuppressants can be used prior to, at the time of, or after introduction of the nerve graft into the individual. See, for example, Scharpf, J., et al., *Microsurgery*, 26:599-607 (2006).

As noted above, the nerve graft produced is maintained under conditions in which nerve tissue is regenerated and/or nerve conduction (partial or complete) between the proximal nerve stump and the distal nerve stump is regained. A variety of methods for determining whether nerve regeneration has occurred are provided herein and these as well as other such methods are known to those of skill in the art. For example, clinical assessments such as a pin-prick (Siemionow, M, et al., *Ann. Plast. Surg.*, 48:281-285 (2002)) test, electrophysiological tests (e.g., somatosensory evoked potential evaluation (SSEP)), histomorphometric evaluations, nerve morphometry and morphology evaluations, Tinel sign, nerve conduction velocity, electromyography (EMG), muscle strength evaluation, etc. can be used (*Surgery of the Peripheral Nerve*, Susan E. MacKinnon and A. Lee Dellon, Thieme Medical Publishers, Inc., New York, 1988).

The epineural sheath of autologous, allogenic, xenogenic or isogenic origin can be harvested in the form of a full sheath, sheath/strips, and/or conduit and applied, for example, as an epineural sheath graft to fill nerve defects; as an epineural sheath patch to cover nerves and neural tissues protect them from scarring after surgery; as an epineural conduit to provide nerve guidance at long gap distances or for coverage of spinal nerves; as dura (e.g., for dura tear) of the spinal cord as well as a patch for coverage of dural and brain defects; and as a combination of these applications (e.g., as a conduit, tube, and patch) for different types of applications in peripheral nerve surgery, plastic surgery, orthopedics, vascular surgery, spine and neurosurgery.

The epineural sheath is of neural tissue origin, and thus, enhances nerve regeneration compared to other artificial nerve grafts, conduits, patches. The epineural sheath creates less foreign body reaction and is a natural conduit for the tissues of neural origin. As discussed herein, epineural sheaths can be obtained from a variety of sources (e.g., from allogenic sources) and can be cold stored (e.g., cryopreserved) for off shelf application. As also shown herein, methods of using epineural sheaths for treating nerve injuries can be combined with bone marrow stromal cells (e.g., of autologous and/or allogenic origin) for enhancement of nerve regeneration. The epineural sheath described herein can be used as a graft, conduit, or patch in, for example, peripheral nerve surgery, spine surgery and neurosurgery.

The epineural sheath is of neural tissue origin which provides nerve regeneration, and likely provides less scarring and foreign body formation when compared to artificial conduits. The epineural sheath likely enhances expression of nerve growth factors, neurotrophic factors and neurotropic factors to promote nerve regeneration and neural tissue healing in the natural microenvironment. As shown herein, the epineural sheath works well in combination with bone marrow stromal cells to enhance nerve regeneration which is particularly important in long nerve defects.

The epineural sheath of the invention is an isolated, naturally occurring, epineural sheath which, e.g., in its form as a tube and/or a patch, does not include vascular components of the sheath such as vasa nervorum, so it is a non-vascularized sheath. It does not include components of tissue response to inflammations such as chemokines, cytokines, or macrophages. In addition, the epineural sheath can be filled with different types of cells including bone marrow derived cells such as bone marrow stromal cells, progenitor cells, mesenchymal stem cells, Schwann cells, fat adipocyte cells, chimeric cells, as well as a combination of nerve growth factors, vascular endothelial growth factor, and anti-inflammatory agents such as steroids like DHEA. In addition, the tube may be filled with pulverized epineural sheath, to enhance regeneration.

Example 1 Repair of Peripheral Nerve Defects with Epineural Sheath Graft

In this study, the potential of using detubulized flat epineural sheath strip for bridging nerve gaps as an alternative to nerve autografting technique was investigated. Nerve gaps were created by removing a 1.2 cm segment of the right sciatic nerves. The epineurium of the removed segment was incised longitudinally and by removing the fascicules, a flat rectangular shaped epineural sheath was obtained. The groups (6 rats of each) repaired with one strip, two-strip and full epineural sheath grafts were compared with the animals repaired with autografts and the untreated groups at 12th week. Toe-spread was better in rats repaired with full sheath grafts and conventional nerve grafts compared to single strip graft at 12th week. Somatosensory evoked potential evaluation demonstrated no significant difference in latencies between conventional and epineural sheath groups. Histomorphometric results of the sections from the animals repaired with autograft, two-strip and full sheath indicated adequate regeneration. This new technique can serve as an alternative to conventional nerve autografting.

Epineural sheath was previously reported for nerve repair using sliding technique, the sleeve technique and recently by the application of the turnover technique, wherein the sleeve has one open end and the opposite end is a continuation of the damaged nerve and both ends are filled with neural structures such as fascicules, etc. This method is used in experimental studies and applies only for the autorepair of transected nerves since the epineural sleeve is an integral part of the repaired nerve and cannot be moved into a different location. In addition, it applies only to repair of nerves with a short gap. It does not apply to larger defects where polyfascicular nerve repair is required and cannot be used as a free sleeve or tube independent from the damaged nerve. (Atabay, K., et al., *Plast. Surg. Forum*, 18:121 (1995);

Siemionow, M., et al., *Ann. Plast. Surg.*, 48:281-285 (2002); Tetik, C., et al., *Ann. Plast. Surg.*, 49:397-403 (2002); Ayhan, S., et al., *J. Reconstr. Microsurg.*, 16:371-378 (2000); Yavuzer, R., et al., *Ann Plast. Surg.*, 48:392-400 (2002); Scharpf, J., et al., *Laryngoscope*, 113:95-101 (2003; Meirer, R., et al., *Ann. Plast. Surg.*, 49:96-103 (2002); Meirer, R., et al., *J. Reconstr. Microsurg.*, 17:625-630 (2001); Demirkan, F., et al., *Ann. Plast. Surg.*, 34:67-72 (1995)).

As shown herein, a new straightforward method of nerve gap repair using detubulized epineural sheath graft for bridging nerve gaps of 12 mm is introduced. This method is an alternative to nerve autograft technique with the advantage of decreased donor site morbidity.

Materials and Methods

Animals

Thirty male 8-10 weeks of inbred Lewis rats (LEW) weighing between 200-225 g (obtained from Harlan Spraque-Dawley, Indianapolis, Ind.) were used in the study. All animals received human care in compliance with the Guide for the care and use of laboratory animals published by the National Institute of Health. The rats were anesthetized by intraperitoneal pentobarbital (40 mg/kg) administration. All surgical procedures were performed by the same surgeon using the same microsurgical technique under operating microscope magnification (Zeiss OP-MI 6 SD, Carl Zeiss, Goettingen, Germany). Following surgery, animals were caged individually and were maintained in an environment with a 12-hour light/dark cycle. Water and standard laboratory food was provided ad libitum.

Surgical Technique

The right sciatic nerves were exposed by an oblique gluteal incision and muscle splitting technique from the sciatic notch distal to the bifurcation of the tibial and peroneal branches. The left sides were not operated and were used as controls. The nerve was transected just distal to sciatic notch and proximal to its bifurcation, and 1.2 cm segment of the sciatic nerve was removed (FIGS. 1A-1F and 2A-2E). The epineurium of the removed nerve segment was incised longitudinally and the fascicules of the nerve were removed and a flat rectangular shaped epineural sheath graft was created.

Experimental Groups

Group 1 (n=6)

After resection of the 1.2 cm segment of the sciatic nerve, the defect was left without repair. This group served as a control.

Group 2 (n=6)

The removed sciatic nerve segment was sutured back using standard epineural technique with 4 interrupted 10/0 nylon sutures placed 90 degrees apart.

Group 3 (n=6)

The flat rectangular epineurial sheath graft was splitted longitudinally into two epineural strips and one strip was used to bridge the nerve defect. The single epineural strip was secured to the proximal and distal stumps of the sciatic nerve by one centrally placed horizontal mattress suture using 10/0 nylon suture (FIG. 3A).

Group 4 (n=6)

After longitudinal splitting of the epineurium, both epineural strips were used as a graft to repair the created defect. The strips were sutured to both ends of the sciatic nerve and placed 180 degrees apart from each other. Each graft was secured by one epineural 10/0 nylon suture (FIG. 3B).

Group 5 (n=6)

The flat rectangular epineural sheath was used to repair the defect as a full graft without longitudinal splitting. The sheath was sutured to the proximal and distal stumps with two epineural sutures placed 180 degrees apart (FIG. 3C).

Following nerve repair in all groups, the gluteal fascia and the skin was closed with 4/0 vicryl suture. The animals were observed daily during the first month follow-up and twice a week thereafter.

Evaluation Techniques

Clinical Assessment

The animals were tested by a pin-prick test at 3, 6 and 12 weeks after nerve repair. The pin-prick test was performed by applying pinching stimulus to the hind-limb skin from the knee to the toes and the withdrawal of extremity in response to pain stimulus was regarded as a positive pinch reflex (Siemionow, M., et al., *Ann. Plast. Surg.*, 48:281-285 (2002)). The withdrawal reflex at different regions was graded from 0 to 3, where the absence of withdrawal was accepted as "0", withdrawal in response to the stimulus between knee and ankle was graded as "1", withdrawal at the proximal plantar surface was graded "2", and withdrawal at the toe level was graded "3".

The toe-spread test was evaluated at postoperative weeks 3, 6 and 12 to determine motor recovery after repair. The rats were held up by their tails and their toe-spread movements were graded between 0 and 3. The absence of any movement was graded as "0", the presence of any sign of toe-spread was accepted as grade "1", grade "2" indicated presence of the abduction of the toes and grade "3" was assigned when both the abduction and extension of the toes was present (Siemionow, M., et al., *Ann. Plast. Sung.*, 48:281-285 (2002)).

Electrophysiological Test

Electrophysiological assessment was performed by somatosensory evoked potential evaluation (SSEP) at postoperative weeks 6 and 12 under general anesthesia with intraperitoneal pentobarbital (40 mg/kg). A Bio-logic-A-PAC 486 computer (Bio-logic Systems Corp, Chicago, Ill.) was used for evaluation, which began after the rats were anesthetized with pentobarbital (40 mg/kg intraperitoneal). Stimulating electrodes were placed subcutaneously in the operated hind-limb and the ground electrode to the healthy contralateral hind limb. Using a sagittal incision on the scalp, cranium was exposed by the subperiosteal dissection. Two burr holes were created in the parietal bones of the scull and the recording electrodes were placed to the epidural plane over the mid parietal cortex, the active electrode was placed in the contralateral cortex. The gain of amplifier was set at 3000, with bandpass filter of 30-1500 mHz, stimulation rate of 2.7 cycles/s, stimulus of 100 ms duration, stimulus intensity of 4 to 6 mA, and sweep of 10 msec/div. After 300 trials the averages were obtained. Testing was then repeated on the other side. The positive and the negative potentials of the waveform morphology in the SSEP measurement were obtained and the initial negative wave was marked as N1 and the following positive wave as P1. The second negative potential was marked as N2. The P1 and N2 potentials were most robust and consistent potentials, therefore P1 and N2 potentials were used for comparison of sensory recovery between the groups.

Histomorphometric Evaluation

Evaluation of Gastrocnemius Muscle Atrophy

In each animal, gastrocnemius muscles were harvested from both sides at 12 weeks after repair and wet muscle weight measurements were taken. After formalin fixation, sections were taken from the cross section of the muscles and routine H&E stained paraffin sections were prepared. Each slide was evaluated by a blinded pathologist for features of atrophy. Also mean muscle fiber diameter and mean muscle fiber cross-sectional area was calculated from each slide using image pro Plus software (Silver Spring, Md., Media Cybernetics).

Evaluation of Nerve Morphometry and Morphology

At postoperative week 12, a 1.5 cm segment of sciatic nerve was harvested including host proximal and distal segment and the connecting graft of the epineural sheath. The harvested nerve was tied to a wooden stick with 9/0 suture at both ends and fixed overnight in buffered 3.7% gluteraldehyde. A 1.5 cm segment of normal sciatic nerve was harvested from the contralateral side and served as the normal control. Sections were taken from the proximal nerve segment, middle segment of the graft and distal segment of the sciatic nerve and were processed in epoxy resin (Spur). Semi thin sections (1 mm) were cut and stained with 1% Toludine Blue.

Sections of normal epineural sheath were also taken before grafting as a control for comparison with the grafted sheaths. Both the semi-thin and conventional paraffin sections were prepared to document normal epineural sheath morphology before engraftment.

Photomicrographs of six representative fields were chosen at X1000 magnification from each slide by a blinded observer. After image capture, grey scale conversion and contrast enhancement, and automatic counting were performed using Image pro plus version 6 (Media Cybernetics: MD). The system was calibrated using a 1 mm graticule (micrometer). The following parameters were evaluated; 1-nerve cross-sectional area (square mm), 2-myelinated nerve density (per mm square), 3-total number of myelinated nerve fibers, 4-axonal diameter (mm) and 5-myelin thickness (mm). A blinded pathologist evaluated each slide for the maintenance of fascicular architecture, presence of macrophages or any other inflammatory cells, presence of nerve debris, fibrosis, neuroma formation, and presence of the foreign body reaction (sutures).

Statistical Analysis

The data was statistically analyzed using Kruskal-Wallis Test for comparison between groups and Mann-Whitney U Test for comparison within groups using SPSS 10.0 for Windows. A two sided p value of less than 0.05 was considered to be statistically significant. The results are expressed as Mean+/−SD.

Results

Functional Evaluation

Pin-Prick Test

In all groups, at 3 weeks after repair, none of the animals responded to the stimulus at plantar surface. At 6 weeks the animals in Group 2 (conventional autografting), Group 4 (two-strip graft) and Group 5 (full sheath graft) showed better recovery when compared to Group 3 (one-strip graft) and showed withdrawal at proximal plantar surface. Withdrawal at the toe level was observed in all groups at 12 postoperative weeks (Table 1). The unoperated animals (Group 1) did not show any sign of functional recovery.

Toe-Spread Test

Figure 4:
FIG. 4 is a photograph showing full recovery at toe-spread at 12 weeks from a rat from full sheath repair group

None of the groups exhibited toe spread at 3 weeks after repair. At 6th week, the animals treated with full epineurial grafts (Group 5) and autografts (Group 2) showed better motor recovery demonstrating abduction of the toes. At 12th week, the animals in Groups 2 (autograft), and 5 (full sheath graft) showed significantly better values for both the abduction and extension of the toes, indicating full regeneration, however, the animals treated with one epineural strip demonstrated only slight movement of the foot without signs of abduction or extension (p<0.01) (FIG. 4) (Table 1). No sign of movement were observed in the non-treated group at 12 weeks.

Somatosensory Evoked Potential

Figure 5:
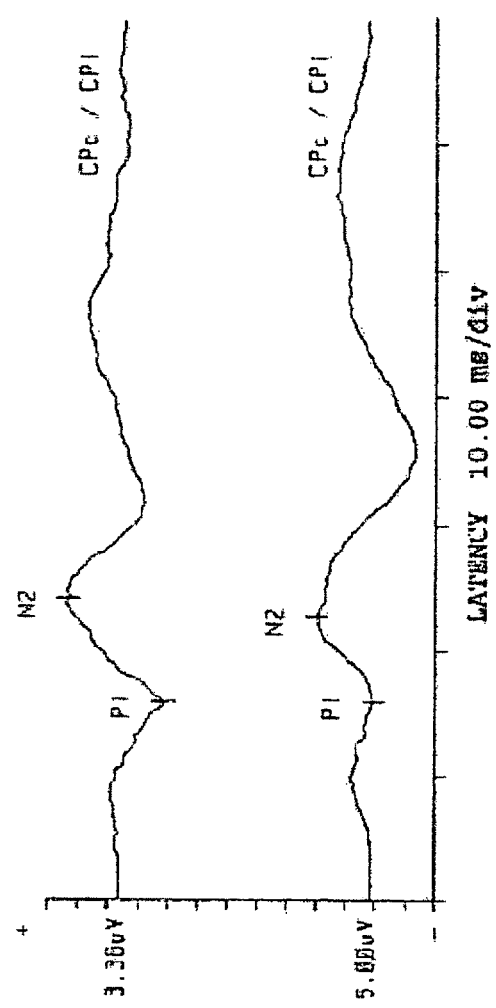
FIG. 5 is a graph showing P1 and N2 latencies obtained by SSEP test in animal repaired with full epineural sheath showing similar waveform patterns. While P1 values were 15.83 ms in the operated side (superior wave) and 15.81 ms in the ipsilateral control limb (inferior wave), N2 latencies were 24.02 ms and 22.66 ms respectively.

The P1 and N2 latency values by SSEP tests are summarized in Table 1. The SSEP evaluations demonstrated non-diagnostic waves at 6th and 12th week postoperatively in the non-treated group. At 6 weeks postoperatively, the P1 and N2 latencies were significantly prolonged in operated limbs in treated groups compared to the contralateral normal limbs. These values were comparable with animals treated with the nerve autograft, full epineural sheath grafts and two-strip grafts (FIG. 5). The latencies did not show improvement in the animals treated with one strip graft, however, there were no statistically significant difference in the P1 and N2 latency values between the treated groups at 12th week.

Histomorphometric Evaluation

Gastrocnemius Muscle Evaluation

Figures 6A, 6B, 6C:
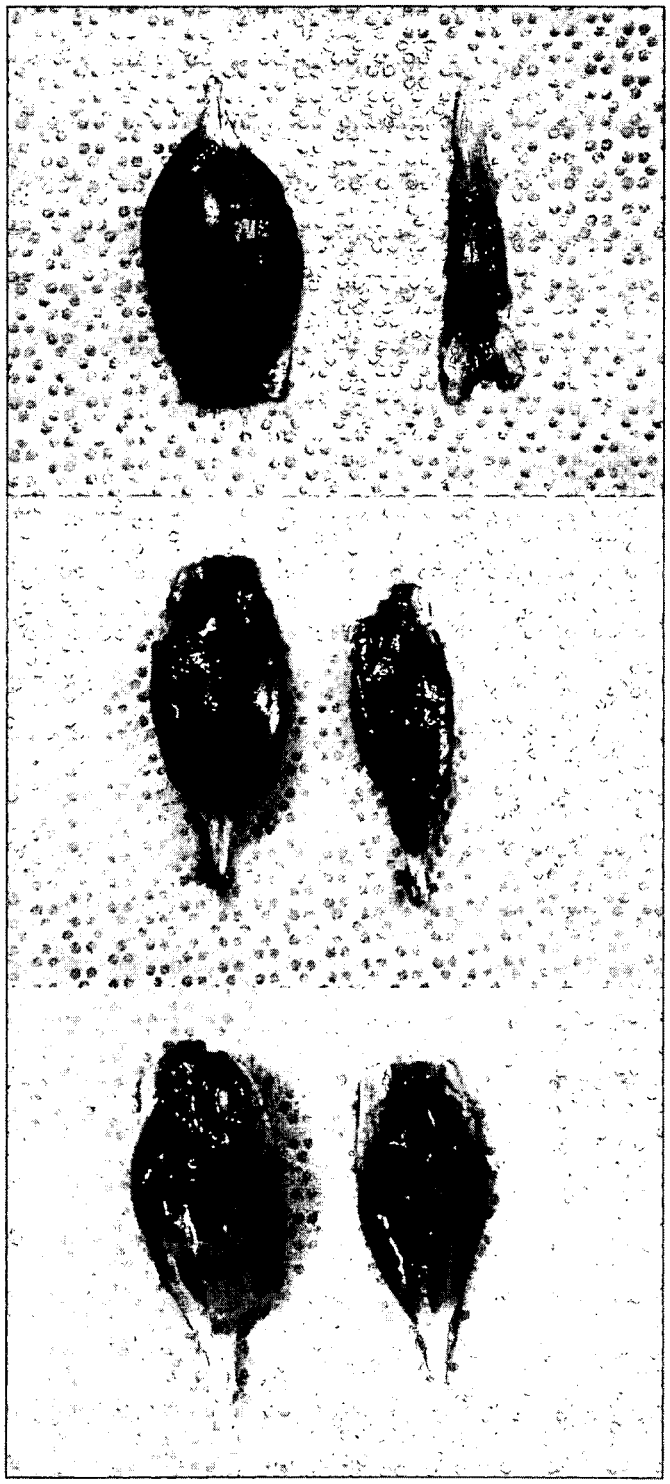
FIGS. 6A-6C are photographs showing gastrocnemius muscles from the non-operated site and operated sites at 12 weeks harvested from one-strip (FIG. 6A), two-strip (FIG. 6B), and full sheath repair group (FIG. 6C). The muscles in the left sides are from non-operated limb and in the right side are muscles from operated limb. Macroscopic atrophy was minimal at the operated site at rats repaired with full rectangular epineural sheath graft.
Figures 7A, 7B, 7C:
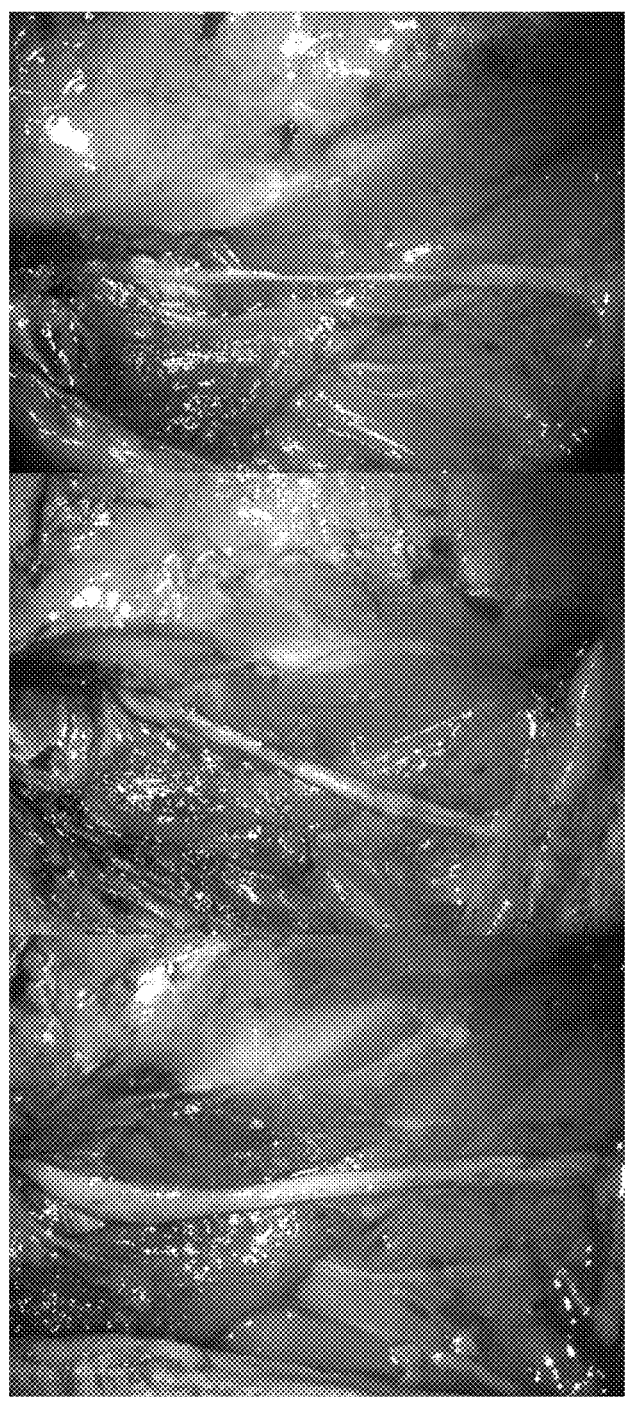
FIGS. 7A-7C are photographs showing the appearance of the grafts from one-strip group (FIG. 7A), two-strip group (FIG. 7B) and full rectangular graft group (FIG. 7C) at 12th weeks prior to harvesting. Only a fibrotic band was observed in one-strip repair group but normal nerve structure was seen at animals repaired with full rectangular sheath graft.
Figures 8A, 8B:
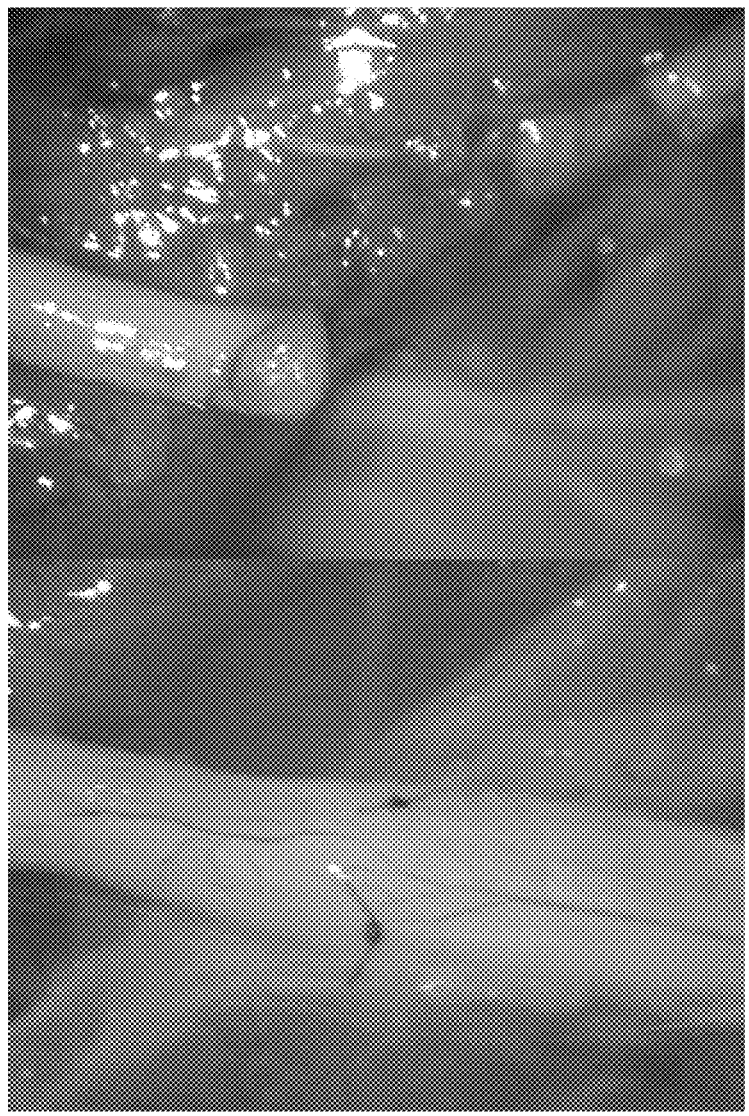
FIGS. 8A-8B are photographs showing (FIG. 8A) a cross section of newly formed nerve in full sheath repair group. Normal nerve structure is observed with outer epineural sheath.

Macroscopically, the gastrocnemius muscle in each group showed atrophy of the muscle fibers (FIGS. 6A-6C). This was reflected by the lower mean fiber diameter and mean fiber surface area values in all three groups compared to the normal control. The extent of the atrophy was more evident in animals treated with the one-strip epineural graft compared to the other treatment groups (p<0.05).

Nerve Histomorphometry

Figures 9A, 9B, 9C:
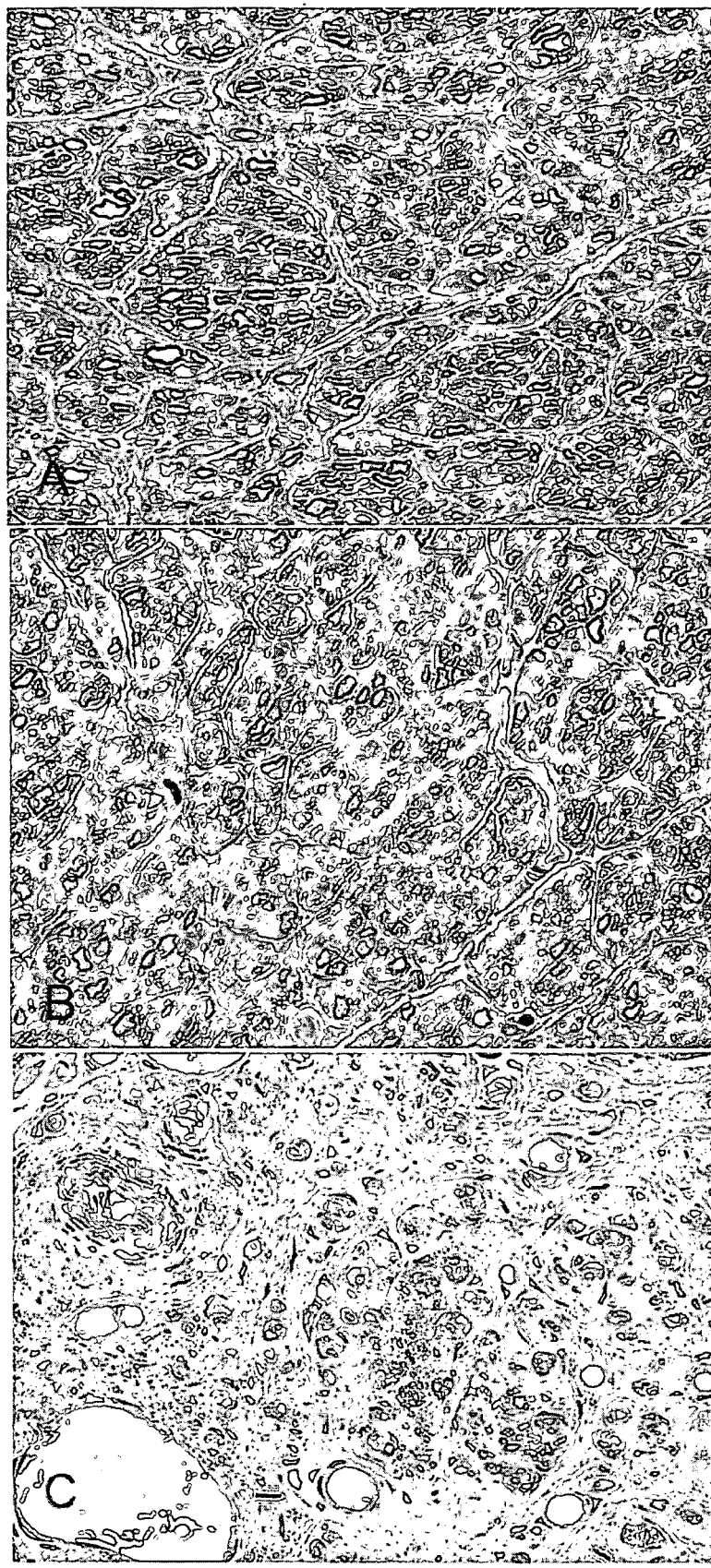
FIGS. 9A-9C show the analysis of the toluidine-blue stained sections from the grafts in animals of (FIG. 9A) Group 5 (full sheath) and (FIG. 9B) of group 4 (two-strip) showing regenerating nerve fibers at postoperative week 12 (magnification ×400).
Figure 10:
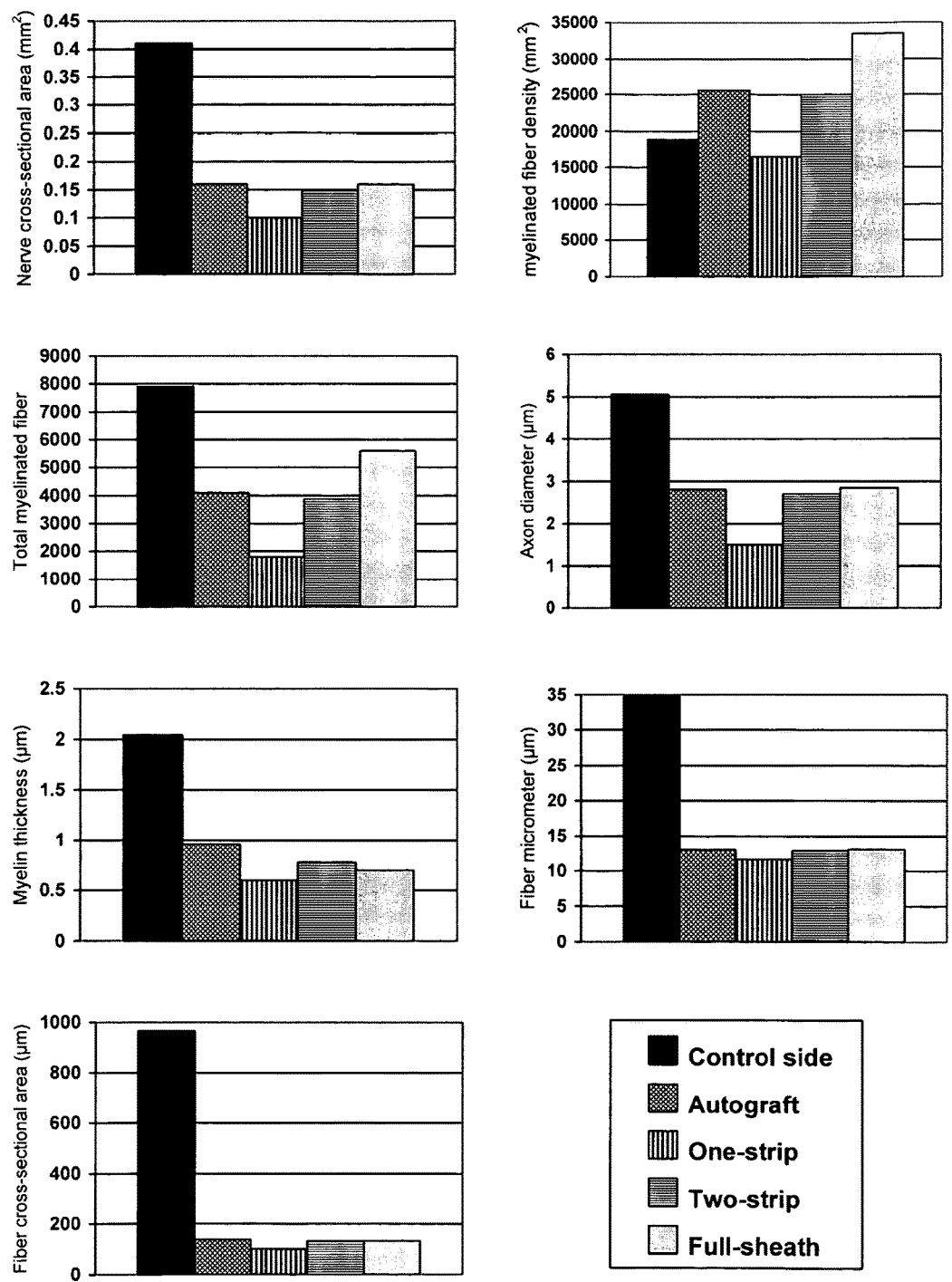
FIG. 10 is a series of graphs showing histomorphometric results.
Figure 11:
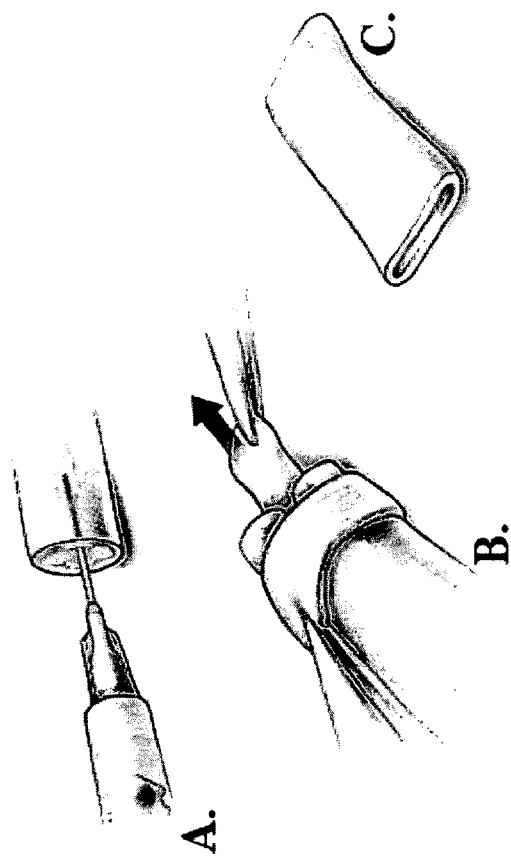
FIG. 11 is a schematic showing the harvest of an epineural tube.

Macroscopic observations of the unrepaired rats showed that there was extensive fibrosis between the nerve stumps without visible neural architecture. In the conventional autograft group, the two-strip graft group and the full sheath graft group there was a normal nerve structure, however the nerves were smaller in diameter compared to the normal control (FIGS. 7A-7C and 8A-8B). The sections taken from the host proximal segment and the contra-lateral normal nerve showed comparable diameter and density of myelinated nerve fibers. In general, the epineural sheath grafts showed reduced nerve cross-sectional area. The sections taken from the graft showed presence of clusters of smaller axons with thin myelin sheath and complementary shape (regenerative clusters) (FIGS. 9A-9C). The axons did not show any fascicular architecture in the graft. There was an absence of inflammatory cells, nerve debris, fibrosis or neuroma formation. The results of histomorphometric analysis are summarized in FIG. 10 and Table 3. Sections from the distal segment showed increased nerve cross-sectional area compared to the epineural sheath graft. There was a presence of the fascicular architecture as well as presence of the extra fascicular regenerative axon clusters. The myelinated axon count in the full epineural sheath grafts and in the two-strip epineural sheath grafts showed a significant increase in the axon count compared to the proximal sciatic nerve segment, which showed typical regenerative response where axons were replaced by the regenerative axon clusters. However, in four out of six animals treated with one-strip epineural graft there was a minimal nerve regeneration presented by a very low numbers of myelinated axon and small diameters of myelinated axons. The other two animals from this group showed adequate nerve regeneration. Nerve cross-sectional area, total number of the myelinated fibers, and the axon diameter were significantly increased in the rats treated with autograft and full sheath grafts compared to the rats treated with one-strip epineural sheath graft (p<0.005). Analysis of the histomorphometric parameters, such as the nerve cross-sectional area, total number of the myelinated fibers, the axon diameter, fiber diameter and fiber cross-sectional area did not show significant difference between the full epineural sheath graft group and the autograft technique groups. Myelinated fiber density was found to be higher in the rats treated with full sheath graft compared to the rats repaired with the autograft (p<0.005). Myelin thickness was significantly higher in the autograft group compared to other groups (p<0.05).

Sections taken from epineural sheath before engraftment showed presence of the fibrocollagenous tissue with the surrounding blood vessels. No Schwann cell was identified histologically.

Discussion

Nerve regeneration is a complex phenomenon involving interaction between the Schwann cells, axons and other cells such as recruited macrophages (Hall, S., *Hand Surg. [Br]*, 26:129-136 (2001)). Following injury, the distal axon and its myelin sheath degenerates and the debris are removed by the recruited macrophages. The Schwann cells de-differentiate leading to the down regulation of the expression of the myelin related m-RNAs and up regulation of the expression of receptors related to the axonally derived ligands and neurotrophins (Scherer, S S, Peripheral neuropathies in "The Molecular and Genetic Basis of Neurologic and Psychiatric Disease". Butterworth-Heinemann; 435-439 (1993)). This phenotype switch of the Schwann cells facilitates axon in-growth and extension. The proliferating and de-differentiating Schwann cells line up within each basal lamina tube to form the bands of Bunger. Meanwhile, a growth cone forms at the viable tip of the distal axon from which multiple axon sprouts emerge in order to occupy the place previously taken by a single large myelinated axon. Such formations are called "regenerative cluster" and are defined in the presence of three or more closely situated myelinated axons. Interaction with the in-growing axons causes a change in the Schwann cell phenotype again, which reverts back to the myelin producing form. Eventually sufficient number of the regenerating axons reaches appropriate target organs for the restoration of function.

In the presence of nerve defect secondary to the peripheral nerve injury, this gap is filled with an exudate that contains blood corpuscles and macrophages forming a fibrin clot. The fluid in the gap has many soluble factors that have high neurotrophic activity of factors secreted by the divided peripheral nerve stumps, which accelerates nerve regeneration (Hudson, T W., et al., *Clin. Plast. Surg.*, 26:485-497 (1999)). During the first few days a fibrin forms a longitudinally oriented matrix bridging the two stumps, in the second week there is an ingrowth of the capillaries, fibroblasts and Schwann cell into the gap zone from both nerve stumps (Hudson, T W., et al., *Clin. Plast. Surg.*, 26:485-497 (1999)). Regenerating axons pass through this matrix and reach the distal stump followed by myelinization. Lack of structures between the nerve ends to guide regenerating axons may cause misdirection of the axons and neuroma formation. It was stated that encasing the stumps of a transected nerve by a tube allows accumulation of locally produced neurotrophic factors (Hazari, A., et al., *Br. J. Plast. Surg*, 52:653-657 (1999)). Lundborg have demonstrated that in the absence of a conduit, regenerating axons fail to reach the distal stump in the presence of 10 mm nerve defect. However, regeneration can occur in 15 mm defect when a silicon chamber is used to bridge the defect (Lundborg, G., et al., *Exp. Neurol.*, 76:361-375 (1982)). If the distal end is left open, regeneration is only partial confirming importance of the distal stump. The target muscles are also important in nerve regenerating as the nerve does not regenerate when the distal segment, which is extending to the corresponding muscle, is resected. This confirms the importance of muscle-nerve interactions. Seckel et al. have shown the importance of the distal nerve stump as a source of the neurotrophic factors by demonstrating failure of regeneration across the gap in the absence of the distal stump or at a distance greater than 10 mm from the proximal stump (Seckel, B R., et al., *Plast. Reconstr. Surg.*, 74:173-181 (1984)). By using Y-configured chambers, MacKinnon et al. have shown that regenerating axons selectively have grown down to the channel of the tube that contained distal nerve stump (Mackinnon, S E, et al., *J Hand Surg. [Am]*, 11:888-894 (1986)). Therefore for the repair of peripheral nerve defects, conduits in the form of the tubulized chambers were used in an attempt to prevent multidirectional axonal sprouting and to help the axons to reach the distal target.

Many different strategies have been developed over the years to facilitate nerve regeneration following injury to peripheral nerve (Siemionow, M., et al., *Neurol. Res.*, 26:218-225 (2004)). Restoration of the peripheral nerves following nerve injury by application of standard nerve grafting technique is limited due to the limited availability of the donor site and the morbidity. Different type of nerve grafts have been used including application of nerve allografts under immunosuppression protocols as well as use of the acellular nerve allografts (Siemionow, M., et al., *Ann. Plast. Surg.*, 24:63-73 (1997); Scharpf, J., et al., *Laryngscope*, 113:95-101 (2003); Meirer, R., et al., *Ann. Plast. Surg.*, 49:96-103 (2002); Doolabh, V B., et al., *Plast. Reconstr. Surg.*, 103:1928-1936 (1999); Kim, B S, et al., *J. Biomed, Mater. Res.*, 68A:201-209 (2004)). The adverse effects of the immunosuppression prevent routine clinical application of the allograft technique in the clinical practice. Significant delay observed during regeneration when using acellular nerve allograft makes this technique not clinically applicable. Other investigations of new procedures facilitating nerve regeneration range from the administration of hyperbaric oxygen and Acetyl-1-carnitine to the use of various types of natural and bioengineered conduits with or without impregnation with nerve growth factors (Zamboni, W A, et al., *J. Reconstr. Microsurg.*, 11:27-29 (1995); McKay Hart, A., et al., *Neurosci. Lett.*, 334:181-185 (2002); Kelleher, M O, et al., *Br. J. plast. Surg.*, 54:53-57 (2001); Midha, R., et al., *J. Neurosurg.*, 99:555-565 (2003)). Described herein is conduit material that causes minimal inflammatory reaction, and serves as a structural guide for regenerating axons and stimulates axonal regeneration along its entire length.

As described herein, whether the bridging of a short nerve gap with the epineural sheath graft is sufficient to sustain nerve regeneration was studied. If the answer is positive, then the question arised if the same technique of epineural sheath grafting process will be adequate enough to be applied to bridge longer nerve gaps. Epineurium was previously used for peripheral nerve repairs in the experimental models in rats (Atabay, K., et al., *Plast. Surg. Forum*, 18:121 (1995); Siemionow, M., et al., *Ann. Plast. Surg.*, 48:281-285 (2002); Tetik, C., et al., *Ann. Plast. Surg.*, 49:397-403 (2002); Ayhan, S., et al., *J. Reconstr. Microsurg.*, 16:371-378 (2000); Yavuzer, R., et al., *Ann Plast. Surg.*, 48:392-400 (2002)). The cooptation side was wrapped by a sliding epineural sheath tube or turnover epineural sheath tube and it was demonstrated that by using this technique there was a less inflammatory reaction with less fibrosis at the cooptation site (Yavuzer, R., et al., *Ann Plast. Surg.*, 48:392-400 (2002)). Epineural sleeve technique, which was first introduced to prevent neuroma formation and facilitate nerve regeneration, was compared with the conventional nerve repair and better functional and histomorphometric results were reported (Siemionow, M., et al., *Ann. Plast. Surg.*, 48:281-285 (2002); Tetik, C., et al., *Ann. Plast. Surg.*, 49:397-403 (2002)). However these experimental models of epineurial sheath application were used in the tubulized form for the primary repair of the transected nerve without a large gap. In the presence of a nerve gap, these sliding or turnover epineural sheath tube models cannot be applied as there will be lack of the nerve segment of the sufficient length to dissect the epineural tube of the distal or proximal nerve stump. It is also impossible to dissect the tube from a distant donor nerve without impairing the nerve's continuity. Finally, the sliding or turnover tubes are always an integral part of the repaired nerve and as such contain normal nerve fascicles inside the tube and cannot be removed from the nerve for distant applications, preservation or storage. Described herein is an epineural sheath grafting model applied for repair of nerve defects. Using a flat full epineural sheath graft, the functional, electrophysiological and histomorphometric outcomes comparable to the conventional repair with the nerve autograft were achieved. Flat rectangular shaped epineural sheath can easily be obtained without impairing nerve continuity. It was shown that harvesting of the epineurium does not alter function of the donor nerve and the donor site is covered by the remaining epineurium after a period required for healing (Yavuzer, R., et al., *Ann Plast. Surg.*, 48:392-400 (2002)). Therefore, this method brings the advantage of eliminating the donor site morbidity such as anesthesia, sensory impairment and neuroma formation, which are the major drawbacks when autografts are used.

As shown herein, detubulized epineural sheath graft provided similar functional recovery and histomorphometric findings compared to the conventional nerve repair with the autograft. The epineural sheath grafts described herein can be used for repair of nerve defects as an alternative method to the autograft technique without donor site morbidity.

TABLE 1

Pin-prick test, toe-spread test, and SSEP evaluation results at postoperative 12th week.

| Groups | Pin-prick | Toe-spread | SSEP (milliseconds (ms)) | | | |
|---|---|---|---|---|---|---|
| | | | Non-Operated site | | Operated Site | |
| | | | P1 | N2 | P1 | N2 |
| Autograft | 3.0 ± 0 | 2.83 ± 0.40 | 16.38 ± 0.89 | 21.56 ± 1.14 | 17.47 ± 1.62 | 24.84 ± 2.14 |
| One-Strip | 2.33 ± 0.51 | 1.16 ± 0.40 | 15.79 ± 0.67 | 22.61 ± 3.00 | 19.06 ± 3.02 | 26.25 ± 2.48 |
| Two-Strip | 2.83 ± 0.40 | 2.0 ± 0.63 | 16.19 ± 1.24 | 22.58 ± 3.10 | 17.47 ± 1.57 | 24.98 ± 2.08 |
| Full Sheath | 2.66 ± 0.51 | 2.16 ± 0.40 | 16.19 ± 0.78 | 22.47 ± 0.84 | 16.24 ± 1.85 | 24.61 ± 2.36 |

TABLE 2

The ratio of wet weight of gastrocnemius muscle in operated site to non operated control side at postoperative 12 weeks

| Groups | WO/WC |
|---|---|
| Conventional | 0.48 ± 0.10 |
| One-Strip | 0.23 ± 0.13 |
| Two-Strip | 0.38 ± 0.09 |
| Full Sheath | 0.47 ± 0.09 |

WO: Wet weight of the gastrocnemius muscle in the operated side
WC: Wet weight of the gastrocnemius muscle in the non-operated contralateral side

TABLE 3

Histomorphometric results in five experimental groups.

| Groups | Nerve Cross-Sectional area (mm²) | Myelinated Fiber Density (mm²) | Total Myelinated Fiber | Axon Diameter (μm) | Myelin Thickness (μm) | Fiber Diameter (μm) | Fiber Corss-Sectional Area (μm) |
|---|---|---|---|---|---|---|---|
| Control Side | 0.41 ± 0.06 | 18936 ± 1520 | 7901 ± 1450 | 5.05 ± 0.16 | 2.04 ± 0.07 | 34.8 ± 0.70 | 965.6 ± 63.5 |
| Conventional | 0.16 ± 0.02 | 25690 ± 773 | 4299 ± 687 | 2.7 ± 0.07 | 0.96 ± 0.10 | 13.0 ± 0.28 | 131.8 ± 6.94 |

TABLE 3-continued

Histomorphometric results in five experimental groups.

| Groups | Nerve Cross-Sectional area (mm$^2$) | Myelinated Fiber Density (mm$^2$) | Total Myelinated Fiber | Axon Diameter (μm) | Myelin Thickness (μm) | Fiber Diameter (μm) | Fiber Corss-Sectional Area (μm) |
|---|---|---|---|---|---|---|---|
| One-Strip | 0.10 ± 0.01 | 16510 ± 12049 | 1795 ± 1453 | 1.5 ± 0.48 | 0.60 ± 0.14 | 11.6 ± 1.44 | 99.3 ± 28.3 |
| Two-Strip | 0.15 ± 0.02 | 25018 ± 3669 | 3868 ± 609 | 2.7 ± 0.53 | 0.78 ± 0.13 | 12.96 ± 0.46 | 130.5 ± 6.6 |
| Full Sheath | 0.16 ± 0.03 | 33550 ± 3472 | 5596 ± 1357 | 2.85 ± 0.51 | 0.70 ± 0.12 | 13.1 ± 0.39 | 131.8 ± 12.9 |

Example 2 Enhancement of Neural Regeneration of Peripheral Nerve Defects by Epineural Tube Graft Enriched with Donor Derived Bone Marrow Stromal Cells Nerve grafting has been the most widely accepted surgical intervention for the repair of peripheral nerve defects. Traditionally however, such interventions have been associated with varying degrees of donor site morbidity. In the search for alternative methods of peripheral nerve repair, the use of biological and artificial materials for the creation of nerve conduits has been investigated. This study described herein was performed to assess the effects of bone marrow stromal cells (BMSC) in nerve gaps repaired with isogenic, isolated epineural tubes filled with isogenic and allogenic BMSCs.

Methods

A total of 54 isolated epineural tubes were harvested. Access to the peripheral nerve e.g. sciatic nerve was made by skin incision and subcutaneous tissue dissection down to the anatomical location of the nerve. At this level the sciatic nerve was cleared of all surrounding tissues by blunt dissection as far proximally as the sacral plexus and as far distally as its division into the terminal nerve branches. All collateral branches arising from the sciatic nerve throughout its length can be detached and used separately to create an epineurial sheath tubular grafts of different size diameters and lengths. At this point the sciatic nerve was ready to be dissected out. The nerve was transected as proximal as was feasible at its origin from the sacral plexus, and then transected distally where the nerve divides into its terminal components, at the level of insertion into the muscle. Depending on the area of nerve harvest the nerve was then suspended/on a either straight driver/irrigator with round tip (e.g. 30 gauge×25 mm depending on nerve diameter—the driver diameter must be smaller than nerve diameter) or on the curved/hook finished driver/irrigator or on screwdriver type of irrigator. The irrigator was filled with chilled solution (either cryopreservation solution for long term storage, or nerve culture medium or combination of both—depending on the fate of graft) and was kept moist on the dissection board by soaking it with 0.9% Sodium Chloride.

Under microscope or loop magnification the axons were then gently teased from its epineural sheath with the use of circular motion of driver/irrigator and jeweler fine forceps pulling the sheath away from the axons and driver in the "devaginating" maneuver—so the axon fibers were pulled from the distal end whilst the epineural sheath was held from the proximal end on the driver/irrigator. Once all axons including perineurium and endoneurium were removed the intact, clear epineural sheath was left as a product of this process and was then inspected for integrity. Two different types of epineural tubes can be made sensory tubes and motor tubes based on the type of nerves from which they were harvested. Different lengths and diameters of epineural sheaths may be obtained by this process based on the nerve diameters.

The epineural tubes were transplanted in 3 experimental groups (18 animals in each group). Group 1 was control saline, Group 2 isogenic (Lew RT1$^1$) BMSCs and Group 3 allogenic (ACI RT1$^a$) BMSCs. The effect of BMSCs and nerve growth factor in epineural conduits was evaluated in a rat sciatic segmental defect model (FIG. 12). In Groups 2 and 3, BMSCs were stained with PKH-26 dye before transplantation, to assess BMSCs nerve engraftment and migration. After staining 2.5-3.0×10$^6$ cells were delivered directly into the transplanted epineural tube. Evaluations were performed at 6, 12 and 18 weeks post-transplant. Sensory and motor recoveries were evaluated by Gastrocnemius Muscle Index (GMI) pinprick, toe-spread and Somato-Sensory Evoked Potentials (SSEP). Axonal counting was performed in addition to immunostaining following nerve growth factors: nerve growth factor (NGF), Laminin B2, glial fibrillary acidic protein (GFAP), and vascular endothelial factor (VEGF) and Von Willebrand Factor for the assessment of the expression of neurotrophic factors and regenerative potential of transplanted BMSCs.

Results 6 weeks post transplantation all groups scored 3 on the pin-prick test. Toe spread for groups 1, 2 and 3 were respectively 1.7; 2; 1. SSEPs in groups 1, 2 and 3 (P1, N2-latencies (milliseconds); P1, N2 percentages (%) of normal values) were respectively (20.2; 23.6; 113; 95), (17.5; 18.1; 98; 73) and (15.7; 21.65; 88; 87). GMIs in groups 1, 2 and 3 were respectively (0.45; 0.48; 0.47). Group 2 showed a higher number of regenerated axons (90.6±26.9) compared to Group 1 (71.4±3.0) and 3 (76.4±5.4).

Figure 13:
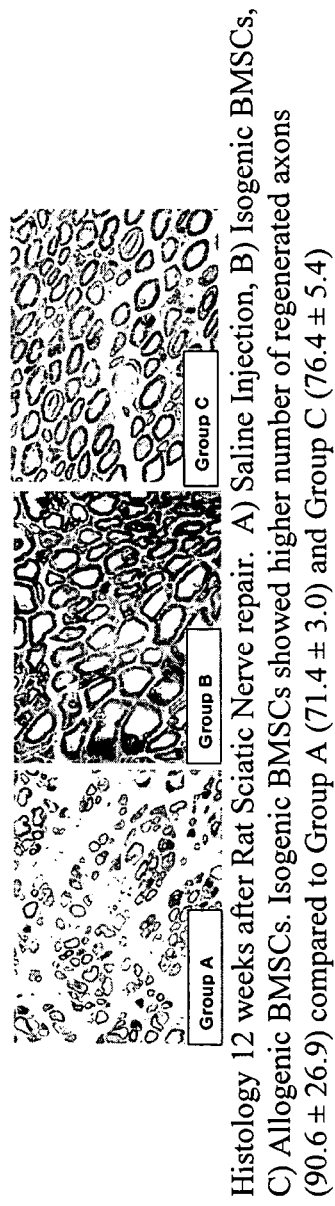
FIG. 13 shows the histology results twelve weeks after rat sciatic nerve repair; Group A: saline injection; Group B: Isogenic BMSCs; Group C: Allogenic BMSCs. Isogenic BMSCs showed higher number of regenerated axons (90.6±26.9) compared to Group A (71.4±3.0) and Group C (76.4±5.4).
Figure 14A:
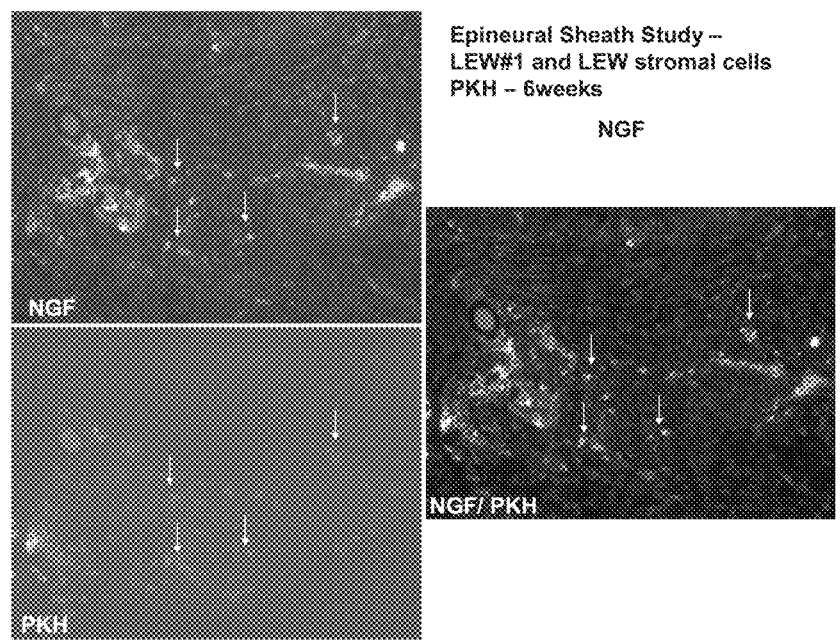
FIG. 14A shows NGF staining 6 weeks after epineural tube transplant supported with isogenic stromal cells, and shows that transplanted cells PKH26 labeled cells are associated with neural marker expression.
Figure 14B:
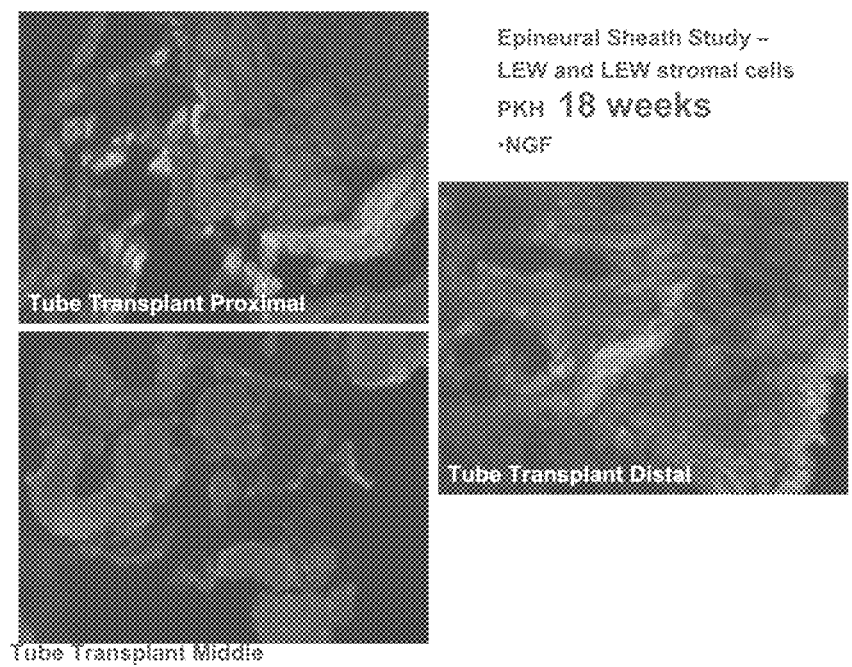
FIG. 14B shows staining at 18 weeks in the distal part of the tube which confirms nerve regeneration over the entire nerve segment from the proximal end to the distal end.
Figure 15:
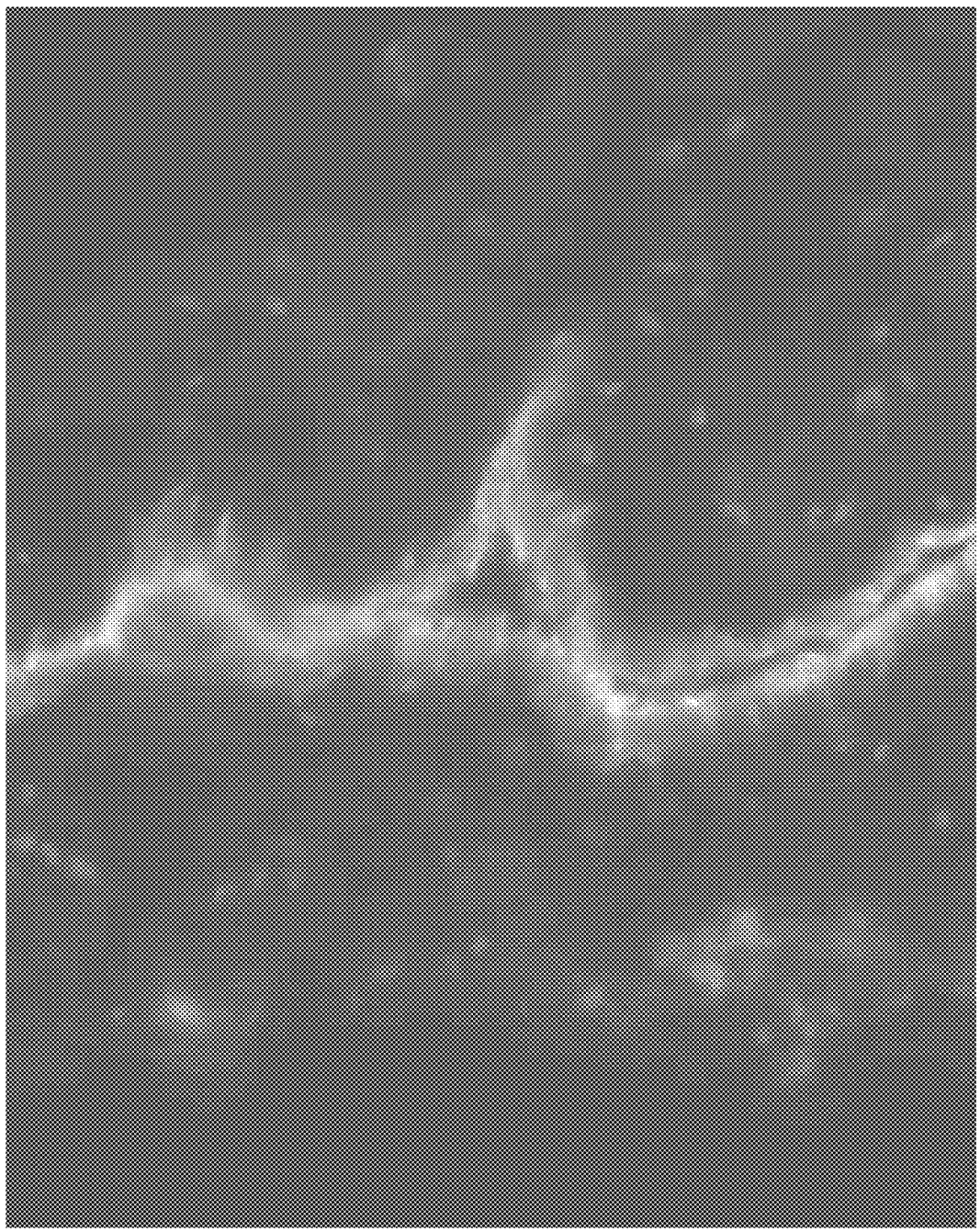
FIG. 15 shows immunostaining results showing laminin B expression in the epineural tube.

Immunostaining with NGF and laminin B2 assessed the expression of neurotrophic factors and the regenerative potential of transplanted BMSCs within the epineural conduits. Histology showed the first signs of axonal regeneration in all groups at 6 weeks. The two groups with BMSCs had PKH26 positive cells in the proximal part of the transplanted epineural conduit. Immunostaining with NGF confirmed upregulation of NGF in the proximal segments of the conduit compared to the middle and distal parts. Differentiation efficacy was greater after transplantation of isogenic BMSCs compared to allogenic BMSCs. NGF upregulation in the MSC-containing groups correlated with upregulation of laminin B2 in both groups, indicating active nerve regeneration. Better functional recovery and axonal regeneration was seen in those epineural conduits that contained BMSCs compared to those that contained only saline. FIG. 12 shows the BMSC processing steps from harvest to implantation, and FIG. 13 shows the histology results for nerve regeneration for the three groups whereas FIG. 14 shows immunostaining for NFG and BMSC and presence of coexpression of NGF/BMSC at 6 weeks at proximal segment of the tube. FIG. 14A shows immunostaining for NFG and BMSC and presence of coexpression of NGF/BMSC at 6 weeks at proximal segment of the tube.

In groups 2 and 3 (with BMSCs) PKH positive cells in addition to NGF, Laminin B2, GFAP, VEGF and Von Willebrand Factor were found in the proximal segment of the transplanted tubes. In contrast, at 18 weeks post transplant isogenic stromal cells (Group 2) expressed neurotrophic factors in the distal portion of the transplanted nerve (see FIG. 14B). This confirmed advancement of nerve growth/regeneration over the entire (previously empty) tube segment over an 18 week period. In the allogenic group (Group 3) neurotrophic factors were expressed in the middle portion of the transplanted nerve indicating slower but advancing growth/regeneration. Coexpression of NGF-staining in combination with PKH-staining confirmed that BMSCs differentiated into neural tissues. Upregulation of Laminin-B2 in both groups indicated active nerve regeneration. Finally, Group 1, the saline control group, showed negative staining for NGF indicating that there is no "spontaneous" nerve regeneration and that BMSC are essential for nerve growth over the empty tube segment.

Conclusion

Co-transplantation of BMSCs within epineural tubes resulted in nerve growth/regeneration over the peripheral nerve defects and confirmed the regenerative potential of BMSCs through their differentiation into and creation of neural tissue. Isogenic BMSCs showed a greater regeneration potential to create neural tissue than allogenic BMSCs. These findings correlated with functional recovery of the nerves as measured by SSEP and axonal regeneration utilizing electron microscopy.

Example 3 Immunostaining of the Epineural Tube

Methods:

The sciatic nerves were harvested from naïve Lewis rats (Lew RT1$^1$). The fascicles were removed using fascicle-stripper device. After fascicle removal empty epineural tube was created. This tube was next evaluated for expression of nerve factors involved in nerve growth and regeneration and was evaluated by monoclonal antibodies and immunofluorescence technique.

Next the cross-sections and longitudinal sections were prepared from whole tubes as well as from tubes split opened and let flat for the testing.

These freshly dissected nerve tubes from naïve Lewis rat were snap-frozen in liquid nitrogen. Prior to immunostaining tissue slides were cut for 5 µm slides and fixed for 10 min. in acetone. Next, sections were rinsed in TBS (Dako) buffer and incubated with mouse anti-rat NGF (H-20), GFAP (2E1), VEGF (C1) (Santa Cruz Biotechnology, Inc), S100 (clone 4C4.9) (LabVision), MHC class II (clone OX-17) and Laminin B (clone D18-2.2) (BD Pharmingen, CA) monoclonal antibodies for 30 min. The binding of primary antibodies was detected using a rabbit anti-mouse immunoglobulin/FITC (DAKO, Carpinteria, Calif., USA) in accordance with the manufacturer's instructions. Slides were mounted in Vectashield mounting medium with DAPI for fluorescence and analyzed using fluorescence microscope.

Results

Only Laminin B was constitutively expressed on the epineurium of the naïve Lewis rats. There was also weak expression of S-100, GFAP and VEGF. In contrast, NGF, MHC class II and VWF were not detected in freshly isolated epineural tubes of naïve rats.

TABLE 4

| Antibody | Cross-Section Epineural Tube | Longitudinal-Section Tube | Longitudinal-Section Flat Tube |
|---|---|---|---|
| NGF | neg | neg | neg |
| Laminin | + | ++ | ++ |
| S100 | w+ | w+ | w+ |
| GFAP | w+ | w+ | w+ |
| VEGF | w+ | w+ | w+ |
| vWF | neg | neg | neg |
| MHC class II | neg | neg | neg | w+ - weak expression

Figure 16:
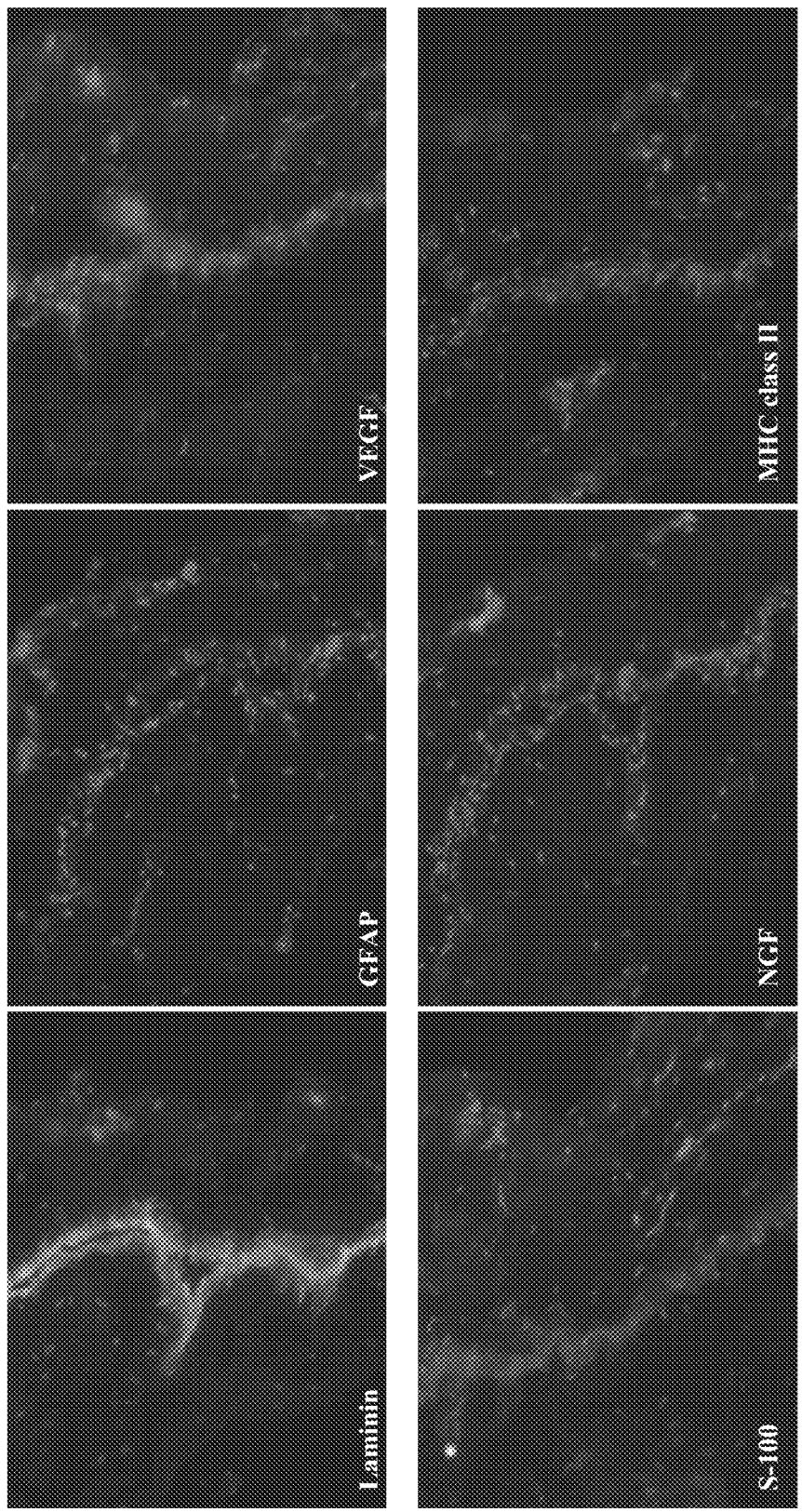
FIG. 16 shows immunostaining results showing laminin, GFAP, VEGF, S-100, NGF and MHC class II expression in the epineural tube.

Immunostaining results showing laminin B expression in the epineural tube are shown in FIG. 16.

Example 4 The Effects of Inflammation on GFAP Expression in Satellite Cells of the Dorsal Root Ganglia Damage to the peripheral nervous system (e.g., peripheral nerves, dorsal root ganglia, and dorsal roots) or the central nervous system (CNS) (e.g., i spinal cord, thalamus) often results in neuropathic pain. Compression of the spinal cord and nerve roots can result in irreversible histological and physiological changes such as intraneural fibrosis, demyelination, and neuronal loss. The mechanism behind these changes is not clearly understood however, it is likely that satellite cells (SC) play a key role. Satellite cells are believed to be neurological cells that closely intact with nerve cells of the dorsal root ganglion (DRG). Satellite cells are connected by gap junctions which are involved in the spatial buffering of extracellular K+ and in neuroprotection.

GFAP expression increases in response to CNS injury, neurodegenerative disease (e.g., Alzheimer's dementia) and aging. Increased expression corresponds to a characteristic cellular hypertrophy referred to as astrogliosis. In the CNS, GFAP plays a key role in modulating astrocytic and neuronal glutamate transporter trafficking and function. Activation of glutamate receptors on astrocytes leads to an increase in intracellular Ca2+. Increased Ca2+ levels results in activation of synaptic receptors and alteration in synaptic transmission.

GFAP is also responsible for maintenance and vascular permeability at the blood-tissue interface. Loss of GFAP impairs Schwann cell proliferation and delays nerve regeneration after injury. GFAP is also essential for normal white matter architecture and blood-brain barrier integrity, and its absence leads to late-onset CNS dysmyelination.

Astrocytes synthesize and release factors, such as colony-stimulating Factor (CSF) or chemokines (e.g., CCR2 ligand) which induces microglial activation. Microglia can synthesize and release IL-1b, IL-6 and TGF-β which play a role in pain sensitization, presumably via a spinal mechanism.

The effects of inflammation on the expression of GFAP in satellite cells of the dorsal root ganglion were tested. Satellite cells are involved in the pathogenesis of neuropathic pain.

Methods/Materials lumbar radiculopathy model (Kawakami, M., et al., *Spine*, 19(16):1780-1794 (Aug. 15, 1994))

96 adult Lewis rats underwent a hemilaminectomy; the contralateral side was not exposed cat gut suture was place topically on the exposed DRG animals were then sacrificed at 6 hrs, 24 hrs, 48 hrs, 72 hrs and 7 days post operatively and their DRG harvested all NC and SC were counted GFAP expression was assessed by counting all SC that express GFAP and dividing them by the total number of SC Results 164 DRGs were harvested and available for analysis naïve controls did not express GFAP GFAP expression was observed in 30% of SC and SC sheaths at 6 hrs GFAP expression was observed 85% of SC and SC sheaths at 24 hrs GFAP expression was observed in 100% 48 hrs, 72 hrs and 7 days SC and SC sheaths in the contralateral internal controls 5% of SC and SC sheaths expressed GFAP at 6 hrs 20% controls at 24 hrs 30% controls at 48 hrs 100% controls at 72 hrs and 7 days Discussion increase in GFAP expression by SC leads to activation of the glutamate receptor this leads to microglia activation and cytokine release this study supports the role of satellite cells in the development and maintenance of nerve injury-induced neuropathic pain Conclusion under physiologic conditions, the expression of GFAP by SC is undetectable by immunohistochemistry as the inflammation process develops, GFAP expression increases, with 30% of SC at 6 hrs and 85% of SC at 24 hrs being GFAP immunoreactive neither the contralateral internal control nor the sham group display such a profound increase in GFAP immunoreactivity at 6 hrs and 24 hrs.

Example 5 Use of the Epineural Sheath as a Patch

Compression of the spinal cord and nerve roots can result in irreversible histological and physiological changes such as intraneural fibrosis, demyelination, and neuronal loss. The epineural sheaths described herein can be used as a protective anti-inflammatory sheath in patients undergoing decompression procedures for myelopathy secondary to, e.g., sponylosis, disc herniation, trauma, tumor and/or complications associated with diabetes.

For example, an epineural sheath of the desired size is placed topically on the exposed dura. The sheath uses the surface properties of the sheath-dura interface to adhere to the dura. Alternatively, glue or suture can be used selectively to enhance epineural sheath adhesion.

The epineural sheaths described herein can also be used to increase neural regeneration in patients undergoing decompression procedures for myelopathy secondary to e.g., spondylosis, disc herniation, trauma, tumor, and/or complications associated with diabetes.

For example, an epineural sheath of the desired size is placed topically on the exposed dura. The sheath uses the surface properties of the sheath-dura interface to adhere to the dura. Alternatively, glue is used selectively to enhance epineural sheath adhesion.

The epineural sheaths described herein can also be used as a dura mater substitute in cases of e.g., dural deficit, iatrogenic durotomy, and/or dural transplant For example, a patch of desired size is cut out of a premade epineural sheath. This patch is then secured into place using sutures/staple/glue.

The epineural sheaths described herein can also be used to prevent scarring and adhesions in patients e.g., undergoing decompressive procedures of the spinal cord, thecal sac, and or nerve roots, and/or in patients suffering from radiculopathy.

The epineural sheath of desired size described herein is placed topically on the exposed dura. The sheath uses the surface properties of the sheath-dura interface to adhere to the dura. Alternatively, glue could is used selectively to enhance epineural sheath adhesion.

The epineural sheaths described herein can also be used to increase neuronal regeneration and decrease inflammation in patients with radiculopathy (e.g., injectable form).

The epineural sheath of desired size described herein is placed topically on the exposed dura. The sheath uses the surface properties of the sheath-dura interface to adhere to the dura. Alternatively, glue is used selectively to enhance epineural sheath adhesion.

The epineural sheath described herein can also be used to create an optimal microenvironment and increase neuronal regeneration in patients suffering from spinal cord injury.

The epineural sheath of desired size described herein is placed topically on the exposed dura. The sheath uses the surface properties of the sheath-dura interface to adhere to the dura. Alternatively, glue is used selectively to enhance epineural sheath adhesion.

An examples of a protocol for epineural sheath harvesting is described herein. Patches are created by splitting of the tubular epineural sheath longitudinally. This is done after removal of the axons. The straight stripper-irrigator is inserted into the tubes and the proximal and distal edges of the tube is fixed to the harvesting board. Next, using e.g., a miniscalpel or microscissors, longitudinal transsection is performed under the guidance of the irrigator. Once transsected, the epineural sheath is opened like a book, flattened, checked for integrity and stored either by cryopreservation technique or cold stored in 4 degrees Celsius.

Different lengths and sizes of sheath can be harvested based on nerve length and diameters. Also the patches can be made thicker by multiplying layers of single patches and can be made in larger dimensions by combining several patches together for different dimensions e.g. 2×2 cm 4×4 cm 6×6 cm etc.

Two different types of patches can be made such as sensory patches, motor patches and mixed sensory/motor patches based on the type of nerves from which they were harvested.

Alternatively patches may be created after cryopreservation from the epineural sheath tubes.

Cryopreservation Technique

For long term preservation and storage epineural sheath tubes and patches can be submitted to cryopreservation techniques.

The goal here is two-fold, first it keeps products stored for as long as 10 years or more in the tissue bank or company storing facility.

Second, cryopreservation is reduces immunogenicity of the epineural sheath but at the same time is keeps the integrity and cellular components of the epinerium intact.

An example of a detailed cryopreservation protocol is outlined below.

Cryopreservation Protocol
I. Equipment and Supplies
Media Preparation
1. Sterile 5 ml serological pipets
2. Sterile 10 ml serological pipets
3. Culture media flasks
4. Sterile 100 ml bags (saline bags)—2+3 pcs
5. Sterile nalgene filters 0.2 mm
6. Needle 20 G—2+3 pcs
7. Syringe 20 ml 2+3 pcs
8. Crushed ice
9. Reagents—see point No III.
Epineural Sheath Harvesting as Described Above
Prefreezing Perfusion
1. Infusion pump
2. Infusion lines 2 pcs
3. Culture plate
4. Syringe a 10 ml
5. Long needle (spinal)
6. Sterile forceps
7. Planer temperature-controlled freezer
8. Cryovials (5 ml)
9. Cryocanes
10. Cryosleeves
11. Cryomarkers
12. LN2 Dewar
Post Thawing Perfusion
1. Infusion pump
groin flap cryopreservation protocol 2
2. Infusion lines 3 pcs
3. Warm bath 37° C.
4. Culture plate
5. Sterile falcone container
6. Crushed ice
Reagents
1. Dimethyl sulphoxide (DMSO)
   1.5 M (final concentration)
   Mol. Weight: 78.13
   Sigma-Aldrich, St. Louis, Mo., Catalog #: 15,493-8
2. Leibovitz L-15 medium
   Irvine Scientific, Santa Ana, Calif., Cat #9082
3. Fetal bovine serum (FBS)
   10% (final concentration)
   Irvine Scientific, Santa Ana, Calif., Cat #3000
4. Sucrose
   0.25, 0.1 M (final concentration)
   Mol. Weight: 342.3
   Sigma-Aldrich, St. Louis, Mo. Cat #S-7903
5. Lactated Ringer's solution: Heparinized (5 U/ml)
II. Preparation of Reagents
Use Sterile Technique
To prepare 100 ml of Cryoprotective Media:
   Transfer 79.36 ml of Leibovitz L-15 media to a sterile flask.
   Add 10 ml of inactivated FBS and mix (55° C. for 30 minutes)
   Add 10.64 ml of DMSO and mix
   Filter media through Nalgene Filters (0.2 mm)
   Place media in the refrigerator until needed
   Transfer to sterile empty bag for infusion
Tissue Preparation
   Transfer some of the Leibovitz media to another sterile tube for transport to OR, keep media cold, and provide sterile 150 mm×25 mm sterile culture dishes
   Flap with a pedicle are harvested, cannulated in Microsurgery lab and delivered to Cryopreservation lab.
   The tissue is placed in sterile culture dish containing the cold media
   The tissues are transported on ice
Infusion System Set-UP
   Set-up the infusion line to infusion system
   Connect infusion system into the cannula through the artery
   Infusion rate: 80 ml/h
   Limit of infusion pressure: 200 mmHg
Start of Perfusion on the Ice
   Perfuse with Heparinized (5 IU/ml) Ringer's solution (room temperature)
till the fluid comes out from the vein for 10 minutes.
groin flap cryopreservation protocol 3
   Perfuse with the Cryoprotectant (0.75 M DMSO+10% FBS in Leibovitz L-15 media) for 15 minutes
   Perfuse with the Cryoprotectant (1.5 M DMSO+10% FBS in Leibovitz L-15 media) for 15 minutes
III. Preparation to Cryopreservation
1. Place Tissue to Cryovials
2. Label 5 ml cryovials with tissue #, date, and other information
3. Add 1 ml of cold cryoprotectant to each tube
4. Transfer one flap to each tube
5. Fill up the cryovial with cryoprotectant solution
6. Transfer vials to Programmed Planer Freezer
IV. Planer Freezer Set-Up
   Connect the liquid nitrogen hose to the LN2 tank. Turn the knob and open the LN2 valve.
   Make sure that the cryochamber is tight and all the four knobs are in the horizontal position
   Switch on Planer Freezer
   The slow freeze settings are:
   Temperature drop down to 4° C.
   Cool at −2° C./min to −7° C.
   Soak for 10 minutes
   Manual seeding,
   Continue to cool at −0.3° C./min to −40° C.
   Cool at a rapid rate of −25° C./min to −140° C.
   Wait for chamber temperature to drop down to 4° C.
   Load specimen vials
V. Long-Term Storage of Issues in the LN2 Tank
   The samples can be stored in LN2 tanks.
cryopreservation protocol 4
VI. Preparation of Reagents for Thawing
Three solutions with different concentration of sucrose are needed
1. 0.25M Sucrose Leibovitz Solution
Transfer 90.0 ml of Leibovitz L-15 media to a sterile flask
Add 0.25 M: 8.56 g of Sucrose
Add 10 ml of FBS in media
Filter media through Nalgene Filters (0.2 mm)
Transfer to sterile empty bag for infusion
2. 0.1M Sucrose Leibovitz Solution
Transfer 90.0 ml of Leibovitz L-15 media to a sterile flask
Add 0.1M: 3.42 g of Sucrose
Add 10 ml of FBS in media
Filter media through Nalgene Filters (0.2 mm)
Transfer to sterile empty bag for infusion
3. Non sucrose Leibovitz solution
Transfer 90.0 ml of Leibovitz L-15 media to a sterile flask
Add 10 ml of FBS in media
Filter media through Nalgene Filters (0.2 mm)
Transfer to sterile empty bag for infusion
Place all media in the refrigerator until needed, transport on ice.

VII. Thawing the Cryopreserved Tissue
1. Remove the Cryovials from the Dewar
2. Hold for 5 minutes in thinsulated container
3. Hold for 5 minutes at room temperature
4. Plunging and swirling in a water bath at 25/37° C. with gentle shaking for 5 minutes
5. Quickly empty the contents of vial into a Petri dish containing Leibovitz L-15 medium with 10% fetal bovine serum
6. Assemble the cannula, tubing and infusion pump
7. Perfuse the flap at a rate 80 ml/h (max pressure 200 mmHg) for 30/45 minutes using 0.25 M, 0.1 M and 0 M Sucrose to remove the cryoprotectant. Perfusion time should be 10/15 minutes for each step.
8. Wash with culture media.
Place in Non sucrose Leibovitz solution for transportation
VIII. Transplantation Technique—Optional
1. Keep sheath immersed in Leibovitz solution
2. Wash with heparinized ringer's lactate solution (5 U/ml)
3. Wash or keep irrigated with neuroprotective (nerve growth factor containing) solution
4. Optionally:
a. Give systemic heparine
b. Give systemic heparine+aspirine
c. Give
Note: Thawing protocol of epineural tissues should be done on ice as described above Example 6 Application of the Epineural Sheath as a Protective Patch for DRG after Laminectomy at L5 Level A dorsal midline incision was made and was carried down sharply to the spinous process of an adult Lewis rat. A combination of sharp and blunt dissection was used to dissect the lumbar musculature over the spinous process and the lamina of L5. Two retractors were placed to retract the dorsal musculature. A rongeour was used to remove posterior bony elements on the left side, exposing the dorsal root ganglia (DRG). The dorsal root ganglia were dissected using microdissectors. The epineural sheath which was harvested from the sciatic nerve of a donor rat of the same species (isogenic) was circumferencially wrapped around the dorsal root ganglia of the L5 on the left side which was exposed. The contralateral side was left intact and the fascia was closed with 4-0 Vicryl and the skin was closed with 4-0 Vicryl as well.

Seventy two hours after patch application, the animals were sacrificed and their DRG and accompanying epineural patch harvested. Frozen sections of epineurium and paraffin sections of epineural patch covering the DRG were stained with a monoclonal antibody for the presence of neural growth factors GFAP, S100 and laminin and for the VEGF expression using immunofluorescence and immunoperoxidase staining respectively.

GFAP and S100 were expressed neither on epineurial sheath nor on epineural sheath patch covering DRG after laminectomy.

Laminin was constitutively expressed on both stained tissues.

Figure 17:
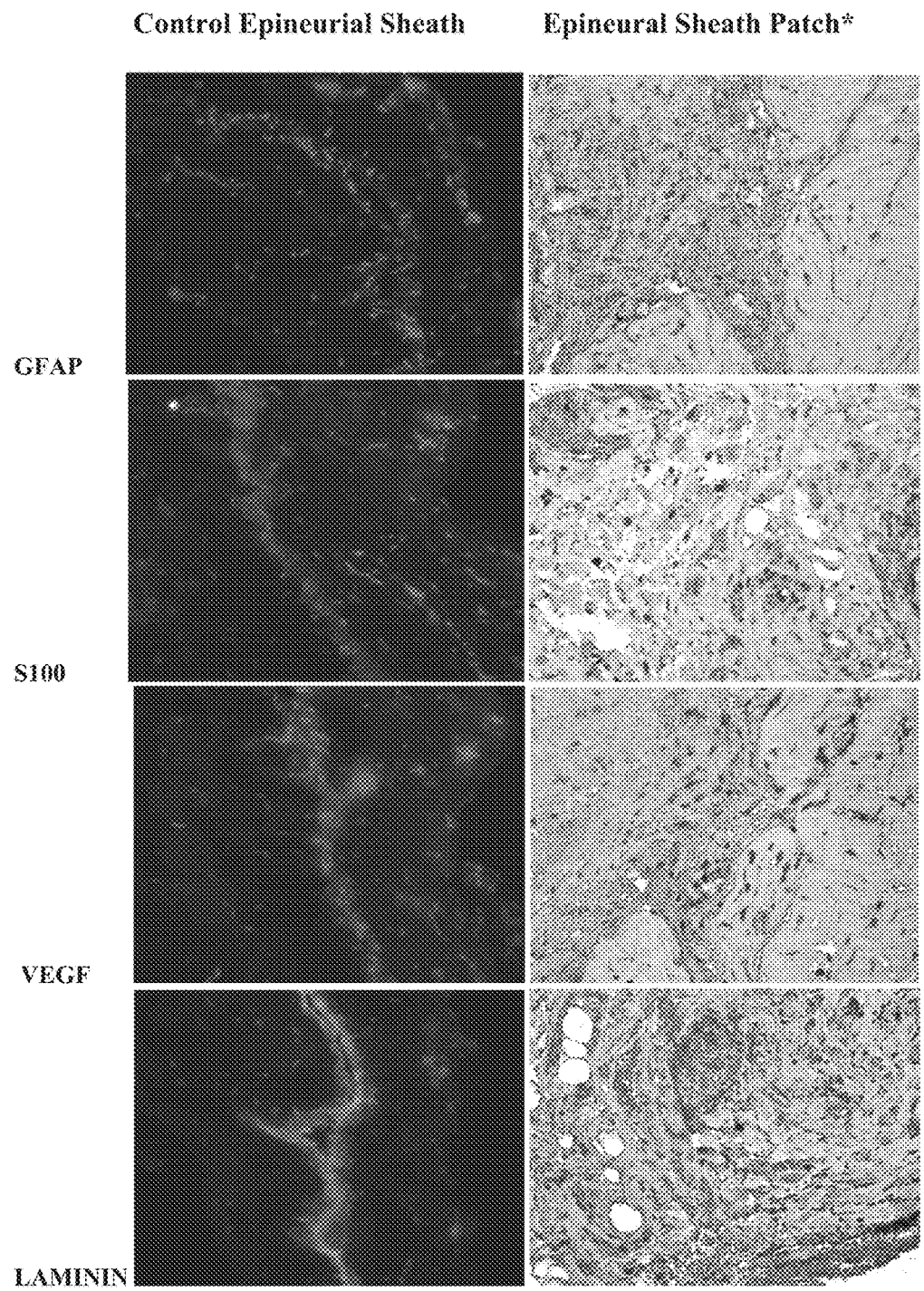
FIG. 17 shows immunostaining and peroxidase staining showing a difference between normal epineural sheath without VEGF expression and epineural sheath patch 72 hours after removal from the dorsal root ganglion indicating VEGF expression and confirming neovascularization potential of the epineural patch.

VEGF was not detected within normal control epineurial sheath. In contrast, in epineural sheaths harvested 72 hours after covering the DRG, numerous VEGF stained vessels were observed. See FIG. 17.

Degenerative spinal changes result in narrowing of the space available for neural structures. This in turn results in nerve ischemia (decrease in blood supply) and intra-neural changes such as fibrosis. It is believed that nerve ischemia leads to altered nerve function and pain.

As shown herein, the epineural sheath has angiogenic properties by demonstrating increased expression of VEGF in the sheath substance 72 hours after topical application onto the DRG.

The epineural sheath cam also be used to increase angioneogenesis (formation of new blood vessels) in chronically compressed lumbar nerve roots by topically applying the epineural sheath (gel, powder, etc) onto the decompressed neural structures (nerve roots, DRG, nerves, dura).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of repairing a nerve gap having a proximal nerve stump and a distal nerve stump in an individual in need thereof, comprising
   a) attaching an isolated, naturally occurring epineural sheath of neural tissue origin to the proximal nerve stump and to the distal nerve stump wherein axons, vascular components, perineurium and endoneurium have been removed from the neural tissue to obtain the isolated, naturally occurring epineural sheath, thereby producing an attached epineural sheath, and contacting the attached epineural sheath with stem cells, thereby producing a nerve graft and
   b) maintaining the nerve graft under conditions in which nerve tissue is regenerated between the proximal nerve stump and the distal nerve stump,
   thereby repairing the nerve gap.

2. The method of claim 1 wherein the epineural sheath is in the form of a tube, a flat sheath, a strip, a patch, a cord, a scaffold, a paste or a powder.

3. A method of repairing a nerve gap having a proximal nerve stump and a distal nerve stump in an individual in need thereof, comprising:
   a) attaching a flat epineural sheath of neural tissue origin to the proximal nerve stump and to the distal nerve stump wherein axons, vascular components, perineurium and endoneurium have been removed from the neural tissue to obtain the isolated, naturally occurring flat epineural sheath, thereby producing an attached epineural sheath, and contacting the attached epineural sheath with stem cells, thereby producing a nerve graft; and
   b) maintaining the nerve graft under conditions in which nerve tissue is regenerated between the proximal nerve stump and the distal nerve stump,
   thereby repairing the nerve gap.

4. The method of claim 3 wherein the flat epineural sheath is attached to the proximal nerve stump using at least one suture and to the distal nerve stump using at least one suture.

5. The method of claim 3 wherein the flat epineural sheath is about 2 cm to about 10 cm in length and about 1 mm to about 10 mm in width.

6. The method of claim 3 wherein the stem cells are bone marrow stem cells.

7. The method of claim 3 wherein the stem cells are bone marrow stem cells, mesenchymal stem cells, dendritic cells, chimeric stem cells or a combination thereof.

8. The method of claim 3 further comprising contacting the nerve graft with nerve growth factors.

9. The method of claim 8 wherein the nerve growth factors are nerve growth factor (NGF), vascular endothelial growth factor (VEGF), BDNGF, INGF, GFAP, laminin B2, cilliary nerve growth factor or a combination thereof.

10. The method of claim 3 wherein the nerve gap is from about 1 mm to about 10 cm.

11. The method of claim 3 wherein the epineural sheath is an autologous epineural sheath, an allogenic epineural sheath, an isogenic epineural sheath, a xenogenic sheath or a combination thereof.

12. The method of claim 11 wherein the allogenic epineural sheath is obtained from a cadaver.

13. The method of claim 3 wherein the epineural sheath is obtained from a sensory nerve or a motor nerve.

14. A method of repairing a nerve gap having a proximal nerve stump and a distal nerve stump in an individual in need thereof, comprising:
   a) attaching at least one epineural strip of neural tissue origin to the proximal nerve stump and to the distal nerve stump wherein axons, vascular components, perineurium and endoneurium have been removed from the neural tissue to obtain an isolated, naturally occurring epineural strip, thereby producing an attached epineural strip, and contacting the attached epineural strip with stem cells, thereby producing a nerve graft; and
   b) maintaining the nerve graft under conditions in which nerve tissue is regenerated between the proximal nerve stump and the distal nerve stump,
   thereby repairing the nerve gap.

15. The method of claim 14 wherein in step a) a first epineural strip and a second epineural strip are each attached to the proximal nerve stump and to the distal nerve stump to produce the nerve graft.

16. The method of claim 15 wherein prior to attaching the first epineural strip and the second epineural strip to the nerve stump, an epineural sheath is split longitudinally, thereby producing a first epineural strip and a second epineural strip.

17. The method of claim 15 wherein the first epineural strip is attached to the proximal nerve stump using at least one suture and to the distal nerve stump using at least one suture, and the second epineural strip is attached to the proximal nerve stump using at least one suture, glue or other adhesive material.

18. The method of claim 15 wherein the each epineural strip is about 1 cm to about 20 cm in length and about 1 mm to about 10 cm in width.

19. The method of claim 15 wherein the stem cells are bone marrow stem cells.

20. The method of claim 15 further comprising contacting the nerve graft with nerve growth factors.

21. The method of claim 20 wherein the nerve growth factors are nerve growth factor (NGF), vascular endothelial growth factor (VEGF), BDNGF, INGF, GFAP, laminin B2, cilliary nerve growth factor or a combination thereof.

22. The method of claim 15 wherein the nerve gap is from about 1 mm to about 10 cm.

23. The method of claim 15 wherein at least one epineural strip is an autologous epineural sheath, an allogenic epineural sheath, an isogenic epineural sheath, a xenogenic sheath or a combination thereof.

24. The method of claim 23 wherein the allogenic epineural sheath is obtained from a cadaver.

25. The method of claim 15 wherein at least one epineural strip is obtained from a sensory nerve or a motor nerve.

26. The method of claim 14 wherein the stem cells are bone marrow stem cells, mesenchymal stem cells, dendritic cells, chimeric stem cells or a combination thereof.

27. A method of repairing a nerve gap having a proximal nerve stump and a distal nerve stump in an individual in need thereof, comprising
   a) attaching an isolated, naturally occurring epineural tube of neural tissue origin to the proximal nerve stump and to the distal nerve stump wherein axons, vascular components, perineurium and endoneurium have been removed from the neural tissue to obtain the isolated, naturally occurring epineural tube and contacting the epineural tube with stem cells, thereby producing a nerve graft and
   b) maintaining the nerve graft under conditions in which nerve tissue is regenerated between the proximal nerve stump and the distal nerve stump,
   thereby repairing the nerve gap.

28. The method of claim 27 wherein the epineural tube is attached to the proximal nerve stump using at least one suture and to the distal nerve stump using at least one suture.

29. The method of claim 27 wherein the epineural tube is from about 1 cm to about 20 cm in length.

30. The method of claim 27 wherein the stem cells are bone marrow stem cells, mesenchymal stem cells, dendritic cells, chimeric stem cells or a combination thereof.

31. The method of claim 27 further comprising contacting the nerve graft with nerve growth factors.

32. The method of claim 31 wherein the nerve growth factors are nerve growth factor (NGF), vascular endothelial growth factor (VEGF), BDNGF, INGF, GFAP, laminin B2, cilliary nerve growth factor or a combination thereof.

33. The method of claim 27 wherein the nerve gap is from about 1 mm to about 20 cm.

34. The method of claim 27 wherein the epineural tube is an autologous epineural tube, an allogenic epineural tube, an isogenic epineural tube, a xenogenic epineural tube or a combination thereof.

35. The method of claim 34 wherein the allogenic epineural tube is obtained from a cadaver.

36. The method of claim 27 wherein the epineural tube is obtained from a sensory nerve, a motor nerve or a mixed sensory/motor nerve.

37. A method of protecting neural tissue in an individual in need thereof, comprising
   a) attaching an isolated, naturally occurring epineural sheath of neural tissue origin to the neural tissue wherein axons, vascular components, perineurium and endoneurium have been removed from the neural tissue to obtain the isolated, naturally occurring epineural sheath, thereby covering the nerve tissue, thereby producing an attached epineural sheath, and contacting the attached epineural sheath with stem cells, and
   b) maintaining the neural tissue under conditions in which the neural tissue is isolated,
   thereby protecting the neural tissue.

38. The method of claim 37 wherein the neural tissue is injured neural tissue.

39. The method of claim 38 wherein the injured neural tissue produces neuropathic pain in the individual.

40. The method of claim 38 wherein the injured neural tissue is compressed.

41. The method of claim 37 wherein neural regeneration occurs.

42. The method of claim 37 wherein the neural tissue is a dorsal root ganglion.

43. The method of claim 37 wherein the epineural sheath is attached to the neural tissue using at least one suture.

44. The method of claim 37 wherein the stem cells are bone marrow stromal cells.

45. The method of claim 37 wherein the stem cells are bone marrow stem cells, mesenchymal stem cells, dendritic cells, chimeric stem cells or a combination thereof.

46. The method of claim 45 further comprising contacting the epineural sheath with nerve growth factors.

47. The method of claim 46 wherein the nerve growth factors are nerve growth factor (NGF), vascular endothelial growth factor (VEGF), BDNGF, INGF, GFAP, laminin B2, cilliary nerve growth factor or a combination thereof.

48. The method of claim 37 wherein the epineural sheath is an autologous epineural sheath, an allogenic epineural sheath, an isogenic epineural sheath, a xenogenic sheath or a combination thereof.

49. The method of claim 48 wherein the allogenic epineural sheath is obtained from a cadaver.

50. The method of claim 37 wherein the epineural sheath is in the form of a patch.

\* \* \* \* \*